United States Patent [19]

Horwell et al.

[11] Patent Number: 5,554,641
[45] Date of Patent: Sep. 10, 1996

[54] NONPEPTIDES AS TACHYKININ ANTAGONISTS

[76] Inventors: David C. Horwell, 8 West Hill, Foxton, Cambridge, England; Martyn C. Pritchard, 9 Bury Close, St. Ives, Cambridgeshire; Jennifer Raphy, 15 Greenhill Park, Thorley Park, Bishops Stortford, Herts CM23 4EW both of United Kingdom

[21] Appl. No.: 406,607

[22] Filed: Mar. 20, 1995

[51] Int. Cl.$^6$ .......................... A61K 31/40; C07D 209/10
[52] U.S. Cl. .......................... 514/415; 514/396; 514/399; 514/231.2; 514/237.5; 514/237.8; 514/238.8; 514/255; 514/408; 514/419; 514/430; 514/443; 514/469; 514/513; 514/595; 544/106; 544/162; 544/170; 544/171; 544/358; 544/382; 544/398; 544/399; 544/400; 544/402; 546/329; 546/339; 546/340; 546/341; 546/342; 548/300.1; 548/335.1; 548/335.5; 548/338.1; 548/340.1; 548/341.1; 548/341.5; 549/29; 549/78; 549/79; 549/49; 549/58; 549/496; 560/19; 560/43; 560/55; 560/61; 560/103; 560/106; 564/47

[58] Field of Search .................... 548/494, 506, 548/300.1, 335.1, 335.5, 338.1, 340.1, 341.1, 341.5; 514/415, 419, 396, 399, 430, 443, 469, 408, 231.2, 237.5, 237.8, 238.8, 255, 513, 595; 549/29, 78, 79, 49, 58, 496; 546/329, 339, 340, 341, 342; 544/106, 162, 170, 171, 358, 382, 398, 399, 400, 402; 560/19, 43, 55, 61, 103, 106; 564/47

[56] References Cited

U.S. PATENT DOCUMENTS 5,348,976  9/1994  Shibata et al. .......................... 514/469

FOREIGN PATENT DOCUMENTS 0310015  3/1989  European Pat. Off. .
3913290  10/1990  Germany .

OTHER PUBLICATIONS

CA 109:6970g Preparation . . . agents. Horwell et al., p. 606, 1988.

P. Boden, et al. *Bioorg & Med Chem Lett*, 1994, 4:14, 1679–1684.

X. Edmonds–Alt, et al., *Life Sci*, 1995, 56:PL 27–32.

*Primary Examiner*—Joseph K. McKane

[57] ABSTRACT

The small nonpeptides of the instant invention are tachykinin antagonists. The compounds are highly selective and functional NK$_3$ antagonists expected to be useful in the treatment of pain, depression, anxiety, panic, schizophrenia, neuralgia, addiction disorders, inflammatory diseases, gastrointestinal disorders, vascular disorders, and neuropathological disorders.

14 Claims, No Drawings

NONPEPTIDES AS TACHYKININ ANTAGONISTS

BACKGROUND OF THE INVENTION

Over the last decade, major advances have been made in the understanding of the biology of the mammalian tachykinin neuropeptides. It is now well established that substance-P (1), neurokinin A (NKA) (2), and neurokinin B (NKB) (3), all of which share a common C-terminal sequence Phe-X-Gly-Leu-Met-$NH_2$, (Nakanishi S., *Physiol. Rev.*, 67:117 (1987)), are widely distributed throughout the periphery and central nervous system (CNS) where they appear to interact with at least three receptor types referred to as $NK_1$, $NK_2$, and $NK_3$, (Guard S., et al., *Neurosci. Int.*, 18:149 (1991)). Substance-P displays highest affinity for $NK_1$ receptors, whereas NKA and NKB bind preferentially to $NK_2$ and $NK_3$ receptors, respectively. Recently, all three receptors have been cloned and sequenced and shown to be members of the G-protein-linked "super family" of receptors (Nakanishi S., *Annu. Rev. Neurosci.*, 14:123 (1991)). A wealth of evidence supports the involvement of tachykinin neuropeptides in a variety of biological activities including pain transmission, vasodilation, smooth muscle contraction, bronchoconstriction, activation of the immune system (inflammatory pain), and neurogenic inflammation (Pernow B., *Pharmacol. Rev.*, 35:85 (1983)). However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B. E., et al., *Current Opinions in Therapeutic Patents*, 1:197 (1991)), most have been developed through the modification and/or deletion of one or more of the amino acids that comprise the endogenous mammalian tachykinins such that the resulting molecules are still peptides that possess poor pharmacokinetic properties and limited in vivo activities.

However, since 1991, a number of high-affinity nonpeptide antagonists have been reported. Snider R. M., et al., (*Science*, 251:435 (1991)), and Garret C., et al., (*Proc. Natl. Acad. Sci.*, 88.:10208 (1991)), described CP-96,345 and RP 67580, respectively, as antagonists at the $NK_1$ receptor, while Advenier C., et al., (*Brit. J. Pharmacol.*, 105:78 (1992)), presented data on SR 48968 showing its high affinity and selectivity for $NK_2$ receptors. More recently Macleod, et al., (*J. Med. Chem.*, 36:2044 (1993)) have published on a novel series of tryptophan derivatives as $NK_1$ receptor antagonists. It is of interest that most of the nonpeptide tachykinin receptor antagonists described to date arose, either directly or indirectly, out of the screening of large compound collections using a robust radioligand binding assay as the primary screen. Recently, FK 888, a "dipeptide" with high affinity for the $NK_1$ receptor was described (Fujii J., et al., *Neuropeptide*, 22:24 (1992)). Only one $NK_3$ receptor selective ligand, SR 142801, has been published on to date (Edmonds-Alt, et al., *Life Sciences*, 56:27 (1995)).

International Publication Numbers WO 93/01169, WO 93/01165, and WO 93/001160 cover certain nonpeptide tachykinin receptor antagonists.

NKB and also $NK_3$ receptors are distributed throughout the periphery and central nervous system (Maggi, et al., *J. Auton. Pharmacol.*, 13:23 (1993)). NKB is believed to mediate a variety of biological actions via the $NK_3$ receptor including gastric acid secretion; appetite regulation; modulation of serotonergic, cholinergic, and dopaminergic systems; smooth muscle contraction and neuronal excitation. Recent publications descriptive of this art include Polidor, et al., *Neuroscience Letts.*, 103:320 (1989); Massi, et al., *Neuroscience Letts.*, 92:341 (1988), and Improta, et al., *Peptides*, 12:1433 (1991). Due to its actions with dopaminergic (Elliott, et al., *Neuropeptides*, 19:119 (1991)), cholinergic (Stoessl, et al., *Psycho. Pharmacol.*, 95:502 (1988)), and serotonergic (Stoessl, et al., *Neuroscience Letts.*, 80:321 (1987)) systems, NKB may play a role in psychotic behavior, memory functions, and depression.

Accordingly, compounds capable of antagonizing the effects of NKB at $NK_3$ receptors will be useful in treating or preventing a variety of disorders including pain, depression, anxiety, panic, schizophrenia, neuralgia, addiction disorders, inflammatory diseases; gastrointestinal disorders including colitis, Crohn's disease, inflammatory bowel disorder, and satiety; vascular disorders such as angina and migraine and neuropathological disorders such as Parkinsonism and Alzheimer's.

Co-pending application Ser. No. 08/346,052 filed Nov. 29, 1994, covers certain peptides of Formula I

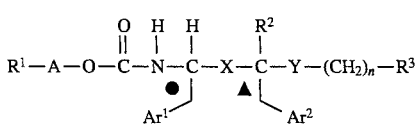

or a pharmaceutically acceptable salt thereof wherein:

$R^1$ is hydrogen,
  $OR^4$,
  $CO_2R^4$,
  cyclo- or polycycloalkyl of from 4 to 10 carbons with from 0 to 3 substituents selected from:
    alkyl,
    halogen,
    $(CH_2)_mCO_2R^4$,
    $(CH_2)_mOR^4$ wherein m is an integer of from 1 to 6 and $R^4$ is hydrogen or alkyl, or
  phenyl unsubstituted or substituted by from 1 to 3 groups selected from:
    alkyl,
    halogen,
    nitro,
    $CF_3$,
    $(CH_2)_pOR^6$,
    $(CH_2)_pCO_2R^6$,
    $(CH_2)_pNR^6R^7$ wherein p is an integer of from 0 to 6 and $R^6$ and $R^7$ are each independently hydrogen or alkyl;

A is —$(CH_2)_q(C(CH_3)_2)_r(CH_2)_s$— wherein q, r, and s are integers of from 0 to 6, 0 to 1, and 0 to 6, respectively;

$Ar^1$ and $Ar^2$ are each independently phenyl unsubstituted or substituted with from 1 to 3 substituents selected from:
  alkyl,
  halogen,
  nitro,
  $CF_3$,
  $(CH_2)_tOR^6$,
  $(CH_2)_tCO_2R^6$, or
  $(CH_2)_tNR^6R^7$ wherein t is an integer of from 0 to 6 and $R^6$ and $R^7$ are each independently hydrogen or alkyl;

X and Y are each independently
  —CONH—,

—CONCH$_3$—,
—COO—,
—CH$_2$NH—,
—NHCO—,
—CH$_2$O—,
—COCH$_2$—, or
—CH$_2$CH—;

n is an integer of from 0 to 10; and

R$^3$ is hydrogen,
straight or branched alkyl of from 3 to 10 carbons with from 0 to 3 substituents selected from:
(CH$_2$)$_n$OR$^8$,
CO$_2$R$^8$,
—NHCOCH$_3$,
—NR$^8$R$^9$,
—SO$_2$Me,
—SOMe,
—SO$_2$NH$_2$,
—CONR$^8$R$^9$,
—NHCONR$^8$R$^9$,
—COR$^4$ wherein n is an integer of from 0 to 6, R$^4$ is as above, R$^8$ and R$^9$ are each independently hydrogen or alkyl,
—guanidine,
—amidine;

R$^3$ is also

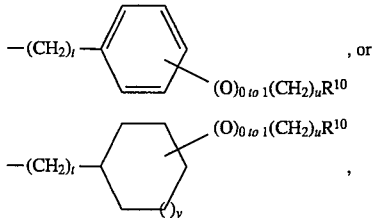

wherein t is an integer of from 0 to 5, v is an integer of from 0 to 2, u is an integer of from 0 to 4, and R$^{10}$ is hydrogen, hydroxy, alkoxy, COOH, CO$_2$alkyl, CONR$^8$R$^9$, NMCONR$^8$R$^9$ guanidine or amidine; and ● and ▲ indicate all stereoisomers.

Copending application Ser. No. 08/344,064 covers certain tachykinin antagonists. It is hereby incorporated by reference.

The compounds of the instant invention provide small molecules which are not peptides; they are monoamino acids in contrast to the dipeptides of the co-pending application. The instant compounds have only one amide linkage and show superior binding affinities.

SUMMARY OF THE INVENTION

The instant invention is novel nonpeptides which are capable of stimulating or blocking the effects of neurokinin B (NKB) at NK$_3$ receptors.

The compounds of the instant invention are those of formula

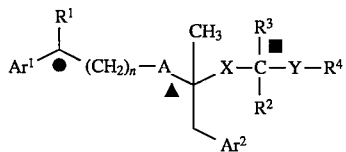

or a pharmaceutical salt thereof wherein Ar$^1$, R$^1$, n, A, Ar$^2$, X, R$^2$, R$^3$, Y, and R$^4$ are as described below.

Pharmaceutical compositions of therapeutically effective amounts of one or more compounds of Formula I and a pharmaceutically acceptable carrier as useful in treating central nervous system disorders such as but not limited to pain, anxiety, depression, and schizophrenia, panic, addiction disorders.

The compounds are also expected to be useful in treating gastrointestinal diseases including but not limited to colitis, Crohn's disease, inflammatory bowel disorder, and satiety.

The compounds are also expected to be useful in treating respiratory disorders such as but not limited to asthma.

The compounds are also expected to be useful in treating inflammation.

The compounds are also expected to be useful in treating circulatory insufficiencies.

DETAILED DESCRIPTION

The compounds of the instant invention are those of Formula I above wherein:

the ●, ▲, and ■ indicate all stereoisomers at these carbon atoms;

Ar$^1$ is phenyl unsubstituted or substituted by from 1 to 3 substituents selected from:
alkyl,
halogen,
nitro,
trifluoromethyl,
cyano,
hydroxy, and
alkoxy;

Ar$^1$ can also be pyridine;

R$^1$ is hydrogen or a straight, branched, or cycloalkyl of from 1 to 7 atoms; or Ar$^1$ and R$^1$ form a ring of 5 to 8 atoms when joined by a bond;

n is an integer of from 0 to 2;

A is OCONH, CONH, CO$_2$, NHCONH, CH$_2$NH, and COCH$_2$;

Ar$^2$ is phenyl as defined in Ar$^1$ above:
pyridine,
thiophene,
naphthyl,
indole,
benzofuran,
benzothiophene, or
imidazole;

X is
—OCONH—,
—CONH—,
—CO$_2$—,
—NHCONH—,
—CH$_2$NH—,
—COCH$_2$—,
—CONCH$_3$—,
—CH$_2$O—,
—CH$_2$CH$_2$—, or
—CH=CH—;

R$^2$ is
hydrogen,
methyl,
phenyl,
benzyl, $CH_2C_6H_{11}$, or

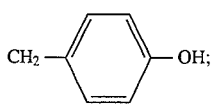

$R^3$ is hydrogen or methyl;

Y is
- $-(CH_2)_m-$,
- $-(CH_2)_mO-$, wherein m is an integer of from 1 to 5,
- $-CONH-$,
- $-CH_2NH-$,
- $-COCH_2-$, or
- $-CH=CH-$; and $R^4$ is hydrogen, alkyl straight or branched of from 1 to 8 atoms unsubstituted or substituted by a substituent selected from:
hydrogen,
$OR^5$,
$NHCOCH_3$,
$NR^5R^6$,
$SO_2CH_3$,
$SO_2NH_2$,
$NHSO_2NH_2$,
$NHCONH_2$,
$CONR^5R^6$,
$COR^5$,

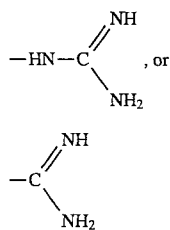

wherein $R^5$ and $R^6$ are each independently hydrogen or alkyl, and $R^4$ is

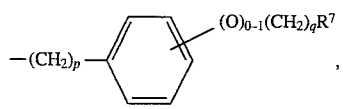

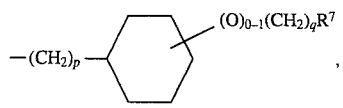

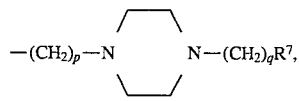

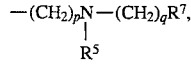

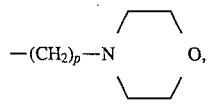

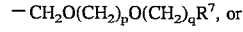

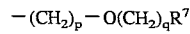

wherein p is an integer of from 0 to 5, q is an integer of from 0 to 4, and $R^7$ is hydrogen, hydroxy, alkoxy, $CONR^5R^6$, or $NHCONR^5R^6$ wherein $R^5$ and $R^6$ are as described above.

Preferred compounds of the instant invention are those of Formula I wherein:

● is S or R, ▲ is R, and ▲ is S; $Ar^1$ is phenyl unsubstituted or substituted with from 1 to 2 substituents selected from:
alkyl,
halogen,
cyano, and
alkoxy;

$R^1$ is a straight, branched, or cyclic alkyl of from 1 to 6 atoms; or $Ar^1$ and $R^1$ form a ring of 7 atoms;

n is an integer of from 0 to 1;

A is OCONH, CONH, NHCONH, or $CH_2NH$;

$A^2$ is phenyl as defined in $Ar^1$ above,
pyridine,
thiophene,
naphthyl, or
benzofuran;

X is
OCONH,
CONH,
NHCONH,
$CH_2NH$,
$CONCH_3$, or
$COCH_2$;

$R^2$ is
hydrogen,
phenyl,
benzyl, or

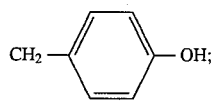

$R^3$ is hydrogen or methyl;

Y is $(CH_2)_m$, CONH, $CH_2NH$, or $COCH_2$;

$R^4$ is hydrogen, alkyl straight or branched of from 3 to 7 atoms with a substituent selected from:
$OR^5$,
$NHCOCH_3$,
$SO_2CH_3$,
$SO_2NH_2$,
$NHSO_2NH_2$,
$NHCONH_2$,
$CONR^5R^6$,
$COR^5$ wherein $R^5$ and $R^6$ are each independently hydrogen or alkyl, and $R^4$ is

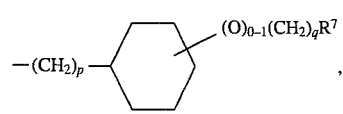

-continued

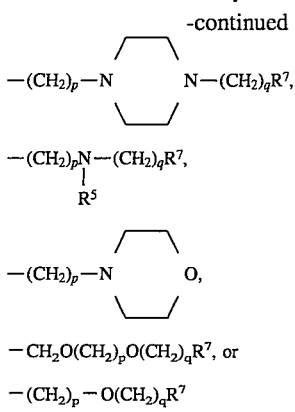

wherein p is an integer of from 0 to 2, q is an integer of from 0 to 3, and $R^7$ is hydroxy, alkoxy, $CONR^5R^6$, or $NHCONR^5R^6$.

More preferred compounds of the instant invention are those of Formula I wherein:

● is S or R, ▲ is R, and ■ is S;

$Ar^1$ is phenyl unsubstituted or substituted by halogen, cyano, or alkyl;

$R^1$ is a branched or cycloalkyl of from 3 to 6 carbon atoms, or $Ar^1$ and $R^1$ are joined to form a ring of 7 atoms;

n is zero;

A is OCONH or NHCONH;

$Ar^2$ is phenyl unsubstituted or substituted by halogen, cyano or alkyl, or $Ar^2$ is thiophene, naphthyl, or benzofuran;

X is $CONH$, $CH_2NH$, or $COCH_2$;

$R^2$ is hydrogen, phenyl or

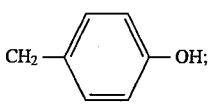

$R^3$ is hydrogen or methyl;

Y is $CH_2$ or CONH;

$R^4$ is hydrogen, alkyl which is a straight chain of from 4 to 6 atoms with a substituent selected from:
hydroxy,
$NHCOCH_3$,
$NHCONH_2$.

Most preferred compounds of the instant invention are those of Formula I named:

Carbamic acid, [2-[(9-amino-9-oxononyl)amino]-1-methyl-2-oxo-1-(phenylmethyl)ethyl]-, 2-methyl- 1-phenylpropyl ester, [R-(R*,S*)]-;

Carbamic acid, [2-[(9-amino-9-oxononyl)amino]- 1-methyl-2-oxo-1-(phenylmethyl)ethyl]-, 1-(4-chlorophenyl)-2-methylpropyl ester;

[1-(8-Carbamoyl-octylcarbamoyl)-1-methyl-2-phenylethyl]-carbamic acid cyclopentyl-phenyl-methyl ester;

[1-(8-Carbamoyl-octylcarbamoyl)-1-methyl-2-phenylethyl]-carbamic acid 6,7,8,9-tetrahydro- 5H-benzocyclohepten-5-yl ester;

[1-(8-Carbamoyl-octylcarbamoyl)-1-methyl-2-phenylethyl]-carbamic acid 2,2-dimethyl-1,2,3,4-tetrahydronaphthalen- 1-yl ester;

Carbamic acid, [1-methyl-2-oxo-2-[(1-phenylethyl)-amino]-1-(phenylmethyl)ethyl]-, (R) or (S)-2-methyl- 1-phenylpropyl ester, [R-(R*,S*)]-;

[1-Methyl-1-(1-methyl-1-phenyl-ethylcarbamoyl)- 2-phenyl-ethyl]-carbamic acid 2-methyl-1-phenyl-propyl ester;

[1-(2-Hydroxy-1-phenyl-ethylcarbamoyl)-1-methyl- 2-phenyl-ethyl]-carbamic acid 2-methyl-1-phenyl-propyl ester;

Carbamic acid, [2-[(8-hydroxyoctyl)amino]- 1-(1H-indol-3-ylmethyl)-1-methyl-2-oxoethyl]-, 2-methyl-1-phenylpropyl ester;

[2-(2-Fluoro-phenyl)-1-methyl-1-(7-ureido-heptylcarbamoyl)-ethyl]-carbamic acid 2-methyl- 1-phenyl-propyl ester;

[2-(2,3-Difluoro-phenyl)-1-methyl-1-(7-ureido-heptylcarbamoyl)-ethyl]-carbamic acid 2-methyl- 1-phenyl-propyl ester;

[1-(8-Carbamoyl-octylcarbamoyl)-1-methyl-2-phenylethyl]-carbamic acid 6,6-dimethyl-6,7,8,9-tetrahydro-5H-benzocyclohepten-5-yl ester;

{1-[1-(6-Hydroxy-hexylcarbamoyl)-2-(4-hydroxy-phenyl)-ethylcarbamoyl]-1-methyl-2-phenyl-ethyl}-carbamic acid 2-methyl-1-phenyl-propyl ester;

{1-[1-(7-Hydroxy-heptylcarbamoyl)-2-(4-hydroxy-phenyl)-ethylcarbamoyl]-1-methyl-2-phenyl-ethyl}-carbamic acid 2-methyl-1-phenyl-propyl ester; and {1-[2-(4-Hydroxy-phenyl)-1-(6-ureido-hexylcarbamoyl)-ethylcarbamoyl]-1-methyl-2-phenyl-ethyl}-carbamic acid 2-methyl-1-phenyl-propyl ester.

The compounds of Formula I are further defined as follows.

The term "alkyl" means a straight or branched hydrocarbon having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, undecyl, dodecyl, and the like unless stated specifically otherwise.

The term "cycloalkyl" means a saturated hydrocarbon ring which contains from 3 to 12 carbon atoms, for example, cyclopropyl, cyclobutyl, cyclopentyl, cyclohexyl except as otherwise specifically stated.

The term "alkoxy" means an alkyl as described above attached through an oxygen.

The term "halogen" is chlorine, fluorine, bromine, or iodine.

The ring formed by the joining of $Ar^1$ and $R^1$ is from 4 to 8 atoms total and is unsubstituted or substituted by one or more substituents selected from methyl, dimethyl, or isopropyl.

The compounds of Formula I are capable of forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see for example, Berge S. M., et al., "Pharmaceutical Salts," *J. of Pharma. Sci.*, 66:1 (1977)).

The acid addition salts of said basic compounds are prepared by contacting the free base form with a sufficient amount of the desired acid to produce the salt in the conventional manner. Preferably, a compound of Formula I can be converted to an acidic salt by treating with an aqueous solution of the desired acid, such that the resulting pH is less than four. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., supra).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than nine. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the instant invention are highly selective and competitive antagonists of the $NK_3$ receptor.

Compounds have been tested in the in vitro central guinea pig medial habenula paradigm and the human $NK_3$ receptor CHO cell functional assay.

TABLE I

| | $NK_3$ Antagonist Activity | |
|---|---|---|
| Example | Guinea Pig Medial Habenula (Ke, nM) | Human $NK_3$ Receptor in CHO Cells (Ke, nM) |
| 8 | 11 | 22 |
| 9 | 5.8 | 0.88 |

The protocols for these two in vitro functional assays are described below. For the guinea pig medial habenula assay, extracellular recordings were made from guinea pig medial habenula neurones in a brain slice preparation in vitro. Compounds were tested for the ability to block senktide-induced increases in firing rate. Parallel shifts to the right of the senktide dose-response curve with no reduction in maximum were taken as an indication of competitive antagonism. Equilibrium constant (Ke) values for the antagonism were obtained from separate experiments and yielded the mean Ke values shown in the final column. None of the compounds tested had any effect on basal neuronal firing rates.

For the functional assay carried out on human $NK_3$ receptors expressed in CHO cells, the protocol is as follows.

CHO cells, up to passage 20, were harvested 1 to 2 days after passaging by trypsinization and centrifugation (2 minutes @ 100 rpm in a Beckman GPR centrifuge), washed twice (1 minutes @ setting 1.5 in a Beckman Microfuge) with calcium-free Krebs-Hepes buffer (24.5 mM Hepes, 98 mM NaCl, 6 mM KCl, 2.5 mM $NaH_2PO_4$, 5 mM Na-pyruvate, 5 mM Na-fumarate, 5 mM Na-glutamate, 11.5 mM glucose, 1 mM $MgCl_2$ and 2 mM glutamine, pH 7.4) and resuspended in a final volume of 1 mL. The cells were bulk-loaded with 2.5 µM Fura-2AM for 1 hour at 37° C. and washed by centrifugation (Beckman Microfuge as before) to remove excess dye. Loaded cells were then incubated at 21° C. for 30 minutes prior to use to allow complete hydrolysis of Fura-2AM. [$CA^{2+}$] levels were determined using a Shimadzu RF-5001-PC spectrofluorophotometer measuring fluorescence emission at 500 nm following excitation at 340/380 nm. Aliquots of cells (~0.7–1×$10^6$ cells) were placed in a cuvette in a total volume of 2 mL, the extracellular calcium raised to 1.3 mM and a baseline recorded before addition of agonists. Where appropriate, test compounds (2 µL) were added 5 minutes prior to the addition of agonist. All compounds were dissolved in DMSO. Each run was calibrated by the addition of 20 µL 10% SDS solution and 30 µL 750 mM EGTA/Hepes (pH 8.0). Results were calculated as described by Grynkiewicz, et al., *J. Biol. Chem.*, 260:3440–3450 (1993).

The compounds of the invention were also evaluated in an $NK_3$ receptor binding assay which is described below.

Chinese hamster ovary cell membranes were prepared on day of use by thawing cells, diluting with culture medium, and centrifuging at 1000 g for 4 minutes. The resulting pellet was resuspended in assay buffer (50 mM Tris, pH 7.4 containing 3 mM $MnCl_2$, 0.02% BSA, 40 µg/L bacitracin, 2 µg/mL chymostatin, 2 µM phosphoramidon, and 4 µg/mL leupeptin), and washed by centrifugation as above. The cells were then resuspended in assay buffer, counted, and volume adjusted as appropriate. The cell suspension was homogenized using a Brinkman polytron (setting 6, 3×10s) and the equivalent of 0.2–0.25 million cells added per tube. For competition studies, membranes were incubated with [$^{125}$I]

-[Mephe⁷]neurokinin B (40–100 pM) in the presence and absence of test compounds for 90 minutes at 22° C. Assays were terminated by filtration under vacuum using a Brandel harvester onto GF/C filters presoaked with 0.1% PEI for at least 2 hours, and cpm bound determined using a gamma counter. In all cases, specific binding was defined by 1 µM senktide.

TABLE II

In Vitro Human $NK_3$ Receptor Binding Data

| Example | $NK_3$ Binding $IC_{50}$ (nM) |
|---------|------------------------------|
| 1  | 52  |
| 2  | 258 |
| 3  | 40  |
| 4  | 102 |
| 5  | 18  |
| 6  | 61  |
| 7  | 43  |
| 8  | 16  |
| 9  | 7.8 |
| 10 | 91  |
| 11 | 30  |
| 12 | 15  |
| 13 | 12  |
| 14 | 74  |
| 15 | 114 |
| 16 | 94  |
| 17 | 982 |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use the highly selective and competitive antagonists of the $NK_3$ receptor, the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

SCHEME 1

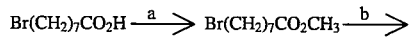

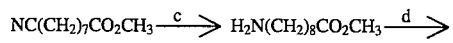

-continued
SCHEME 1

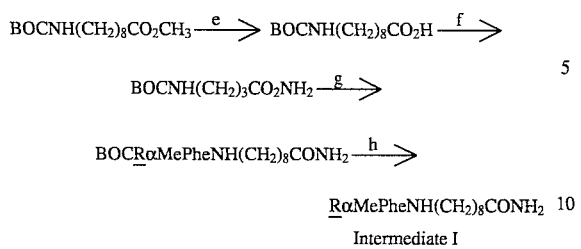

Intermediate I

Reagents and conditions:
a) MeOH, TSOH
b) NaCN, DMSO
c) $NH_3$:MeOH, Ra—Ni
d) $(BOC)_2O$, DMAP, DMF
e) i) LiOH $H_2O$, THF, $H_2O$; ii) 1N HCl
f) i) PFP, DCC, $CH_2Cl_2$; ii) $NH_3$ (g)
g) i) TFA, $CH_2Cl_2$; ii) BOC RαMePheCH, HBTU, DIPEA, DMF
h) TFA, $CH_2Cl_2$.

SCHEME 2

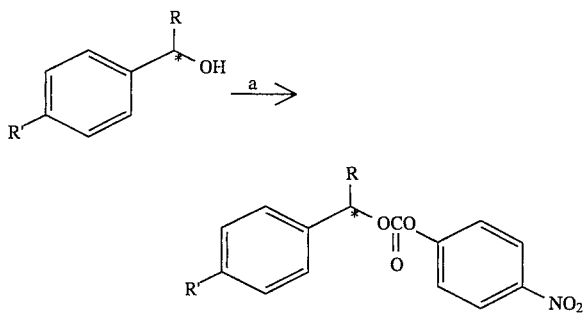

Reagents and conditions:
a) i) R = isopropyl, R' = H, * = S,

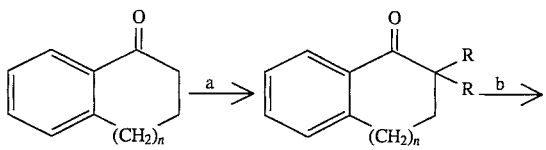

$Et_3N$, THF, Intermediate II.
ii) R = isopropyl, R' = Cl, * = RS,

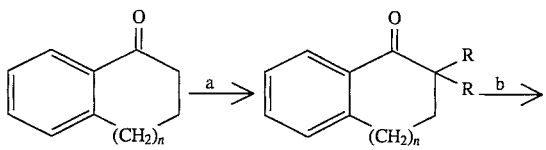

$Et_3N$, THF, Intermediate III.
iii) R = cyclopentyl, R' = H, * = RS,

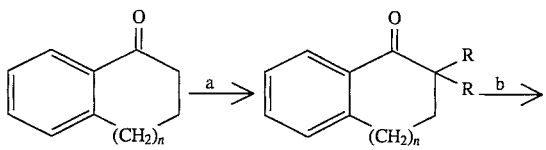

$Et_3N$, THF, Intermediate IV.

SCHEME 3

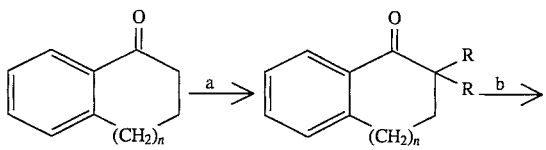

-continued
SCHEME 3

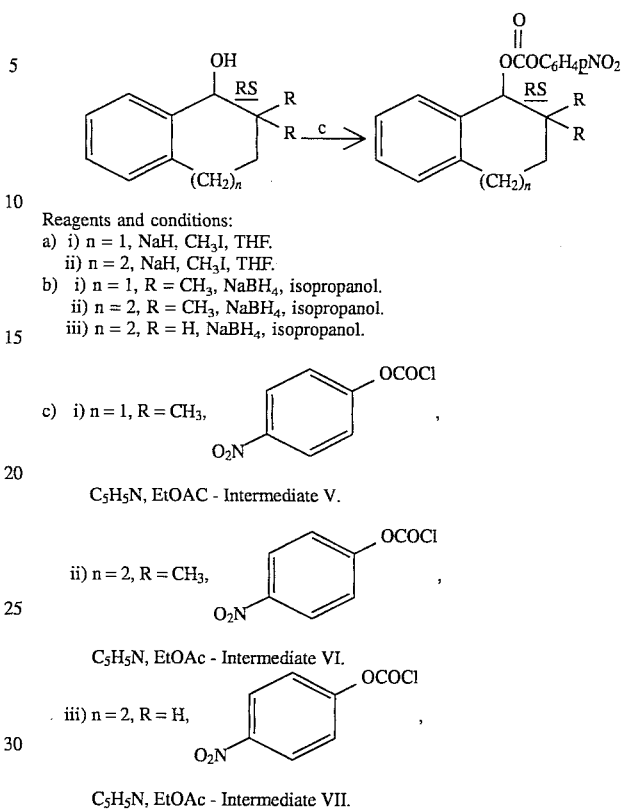

Reagents and conditions:
a) i) n = 1, NaH, $CH_3I$, THF.
   ii) n = 2, NaH, $CH_3I$, THF.
b) i) n = 1, R = $CH_3$, $NaBH_4$, isopropanol.
   ii) n = 2, R = $CH_3$, $NaBH_4$, isopropanol.
   iii) n = 2, R = H, $NaBH_4$, isopropanol.

c) i) n = 1, R = $CH_3$, $C_5H_5N$, EtOAC - Intermediate V.

ii) n = 2, R = $CH_3$, $C_5H_5N$, EtOAc - Intermediate VI.

iii) n = 2, R = H, $C_5H_5N$, EtOAc - Intermediate VII.

Schemes 1 through 3 above describe the synthesis of intermediates required for the preparation of the final compounds as found in the examples.

In Scheme 1, the RαMePheNH$(CH_2)_8$CONH$_2$ intermediate is prepared from readily available 8-bromooctanoic acid. This was achieved by conversion of the acid to methyl ester followed by displacement of the bromine by cyanide and subsequent conversion to the amine using Raney nickel. Protection of the amine with a BOC group followed by base hydrolysis of the ester gave the acid which was converted to the amide by active ester coupling with ammonia. Deprotection of the BOC group followed by active ester coupling with BOC RαMePheOH gave the BOC protected amide which on deprotection gave Intermediate I, RαMePheNH$(CH_2)_8$CONH$_2$ Intermediate IVII.

Scheme 2 describes the synthesis of the carbonate Intermediates II, III, and IV which were prepared by the acylation of the substituted alcohols using p-nitrophenylchloroformate.

The synthesis of the conformationally restricted carbonates V, VI, and VII are described in Scheme 3.

Intermediates V and VI were prepared by dimethylation of the ketone followed by sodium borohydride reduction to the alcohol. Acylation of the alcohol with p-nitrophenylchloroformate in the presence of a base then gave the carbonates. Intermediate VII was prepared similarly from the ketone by reduction followed by acylation of the alcohol.

The synthesis of Examples 1 through 6 are described in Scheme 4. These were each prepared by stirring a solution of the amine Intermediate I in DMF with DMAP and the appropriate carbonate.

SCHEME 4
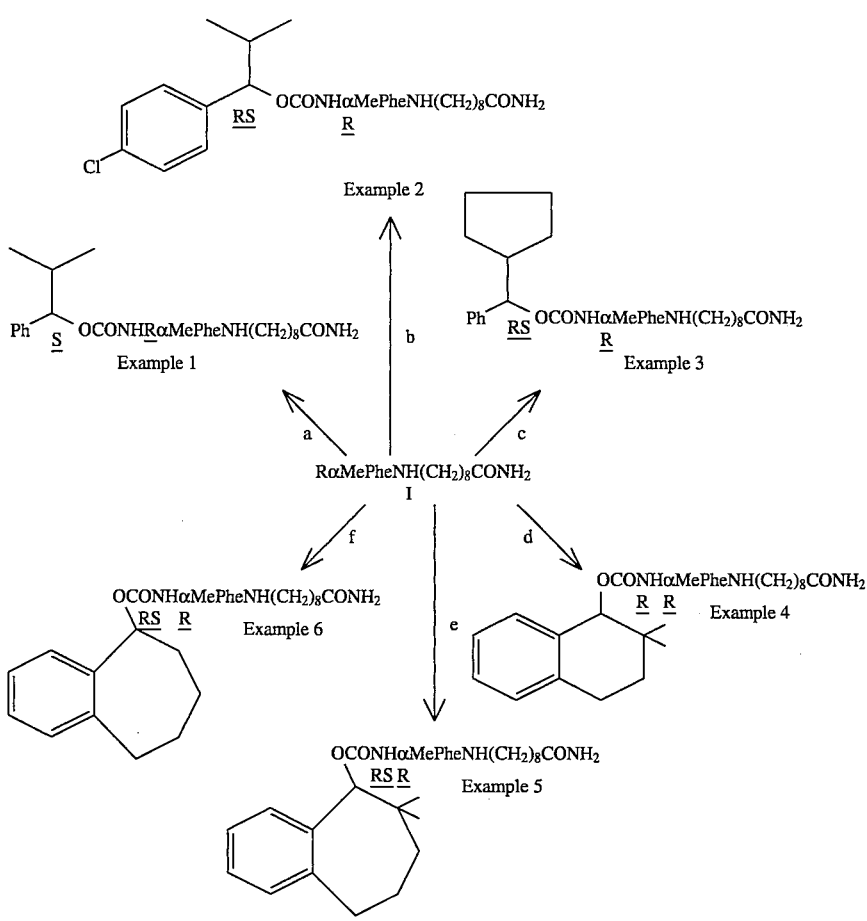
a) Intermediate II, DMAP, DMF
b) Intermediate III, DMAP, DMF
c) Intermediate IV, DMAP, DMF
d) Intermediate V, DMAP, DMF
e) Intermediate VI, DMAP, DMF
f) Intermediate VII, DMAP, DMF
SCHEME 5
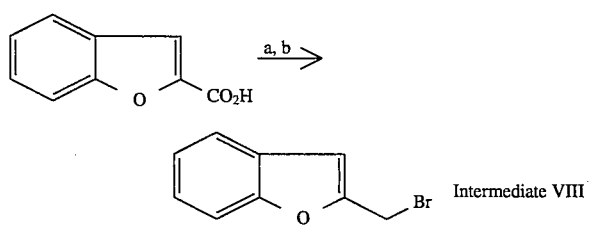
-continued
SCHEME 5
Reagents and conditions:
a) Ethylchloroformate, THF, 4-methylmorpholine, 2 M LiBH$_4$ in THF
b) Triphenylphosphine, Br$_2$, DMF

SCHEME 6

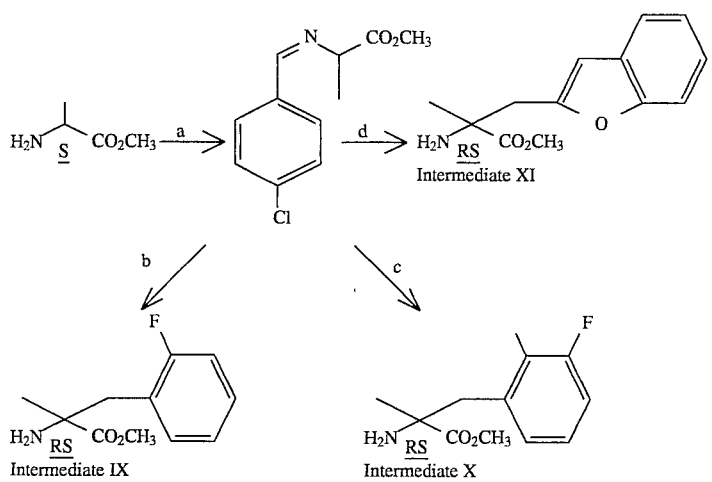

Reagents and conditions:
a) Triethylamine, 4-chlorobenzaldehyde, MgSO$_4$, DCM
b) i) LHMDS, THF, 2-fluorobenzylbromide;
   ii) HCl, H$_2$O
c) i) LHMDS, THF, 2,3-difluorobenzylbromide;
   ii) HCl, H$_2$O
d) i) LHMDS, THF, 2-bromomethylbenzofuran;
   ii) HCl, H$_2$O

SCHEME 7

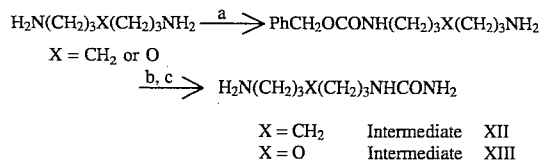

Reagents and conditions:
a) Benzylchloroformate, Na$_2$CO$_3$, 1,4-dioxane, H$_2$O
b) Trimethylsilylisocyanate, THF
c) EtOH, Pearlman's catalyst

SCHEME 8

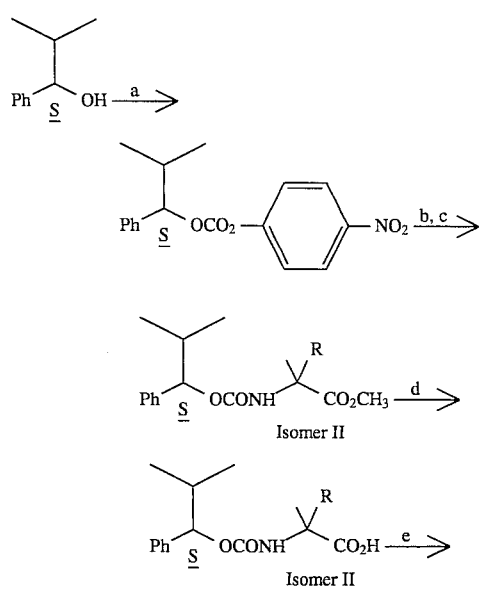

-continued
SCHEME 8

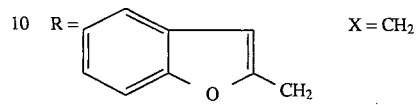

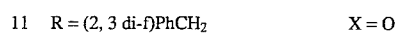

| Example | | |
|---|---|---|
| 7 | R = CH$_2$Ph | X = CH$_2$ |
| 8 | R = (2-f)PhCH$_2$ | X = CH$_2$ |
| 9 | R = (2, 3 di-f)PhCH$_2$ | X = CH$_2$ |
| 10 | R = 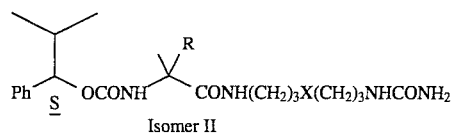 | X = CH$_2$ |
| 11 | R = (2, 3 di-f)PhCH$_2$ | X = O |

Reagents and conditions:
a) 4-Nitrophenylchloroformate, triethylamine, THF
b) Substituted-α-Me-Phe-OCH$_3$, DMF
c) Chromatographic resolution, 10% ether:heptane
d) 1 M LiOH, THF
e) HBTU, DIPEA, DMF, H$_2$N(CH$_2$)$_3$ x (CH$_2$)$_3$NHCONH$_2$ Scheme 5 describes the synthesis of Intermediate VIII via the reduction and subsequent bromination of benzofuran-2-carboxylic acid.

In Scheme 6, the synthesis of Intermediates IX through XI is outlined. The central intermediate Schiff base is prepared from alanine methyl ester via the addition of 4-chlorobenzaldehyde under basic, anhydrous conditions. Alkylation of the Schiff base with 2-fluorobenzylbromide followed by acidic hydrolysis yielded Intermediate IX. Similarly, Intermediates X and XI were isolated via alkylation of the Schiff base with 2,3-difluorobenzylbromide and 2-bromomethylbenzofuran, respectively, followed by acidic hydrolysis.

The synthesis of Intermediates XII and XIII are described in Scheme 7. Both of these intermediates are prepared via initial monoprotection of the diamine starting material with benzylchloroformate followed by preparation of the urea of the unprotected amine using TMS isocyanate with subsequent removal of the benzyl protecting group under reductive conditions.

Scheme 8 outlines the general scheme for the preparation of Examples 7 through 11. Reaction of (S)-1-phenyl-2-methylpropan-1-ol with 4-nitrophenyl chloroformate under basic conditions yielded the reactive carbonate intermediate. This was then reacted with the variously aryl substituted αMePheOMe moieties in DMF to give, in all cases, the urethane as a mixture of diastereomers. The mixture was separated and in each case the slow-running fraction taken on through the synthesis. Base catalyzed hydrolysis of the methyl ester, followed by coupling to either Intermediate XII or XIII, gave Examples 7 through 11.

SCHEME 9

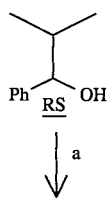

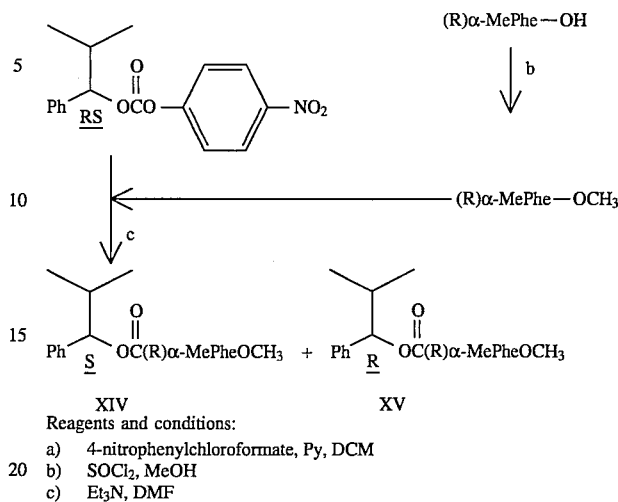

Reagents and conditions:
a) 4-nitrophenylchloroformate, Py, DCM
b) SOCl₂, MeOH
c) Et₃N, DMF Scheme 9 describes the synthesis and chromatographic resolution of Intermediates XIV and XV. The racemic 2-methyl-1-phenyl-1-propanol is converted to a p-nitrophenyl-carbonate. Base promoted coupling to (R)αMePheOCH₃ gave the desired carbamates. (R)αMePheOCH₃ is synthesized from the acid via the use of thionyl chloride and methanol.

SCHEME 10

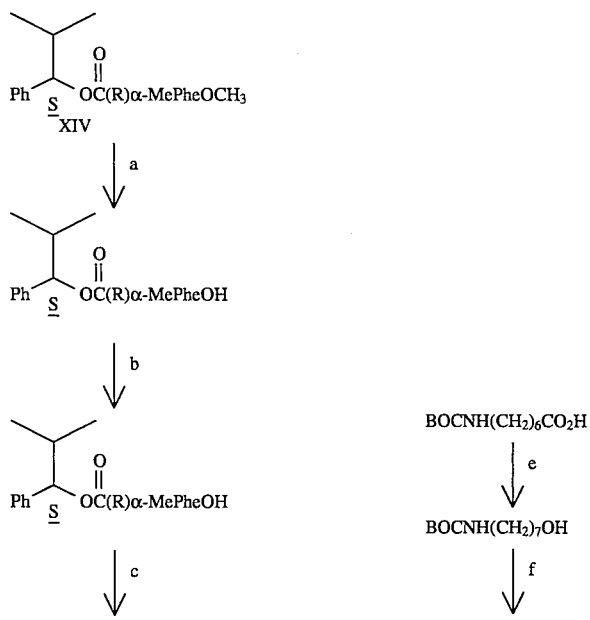

-continued
SCHEME 10

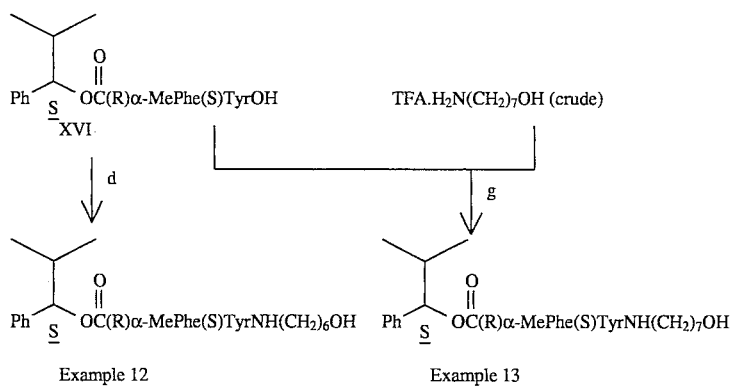

Reagents and conditions:
a) LiOH, THF:H$_2$O
b) HBTU, DIPEA, (S)-TyrOCH$_3$, DMF
c) LiOH, THF:H$_2$O
d) HBTU, DIPEA, H$_2$N(CH$_2$)$_6$OH, DMF
e) i) EtOCOCl, NMM, THF; ii) LiBH$_4$
f) TFA
g) i) HBTU, DIPEA, DMF; ii) K$_2$CO$_3$, H$_2$O, DMF In Scheme 10, Intermediate XIV is hydrolyzed under basic conditions to the carboxylic acid. Coupling to (S)-TyrOCH$_3$ using active ester methodology followed by base catalyzed hydrolysis yields Intermediate XVI.

Example 12 is produced by active ester coupling of Intermediate XVI to 6-amino-1-hexanol.

Example 13 is produced by active ester coupling of Intermediate XVI and the amine salt derived from BOC NH(CH$_2$)$_6$CO$_2$H via reduction of the carboxylic acid to the alcohol and acid catalyzed removal of the BOC group.

SCHEME 11

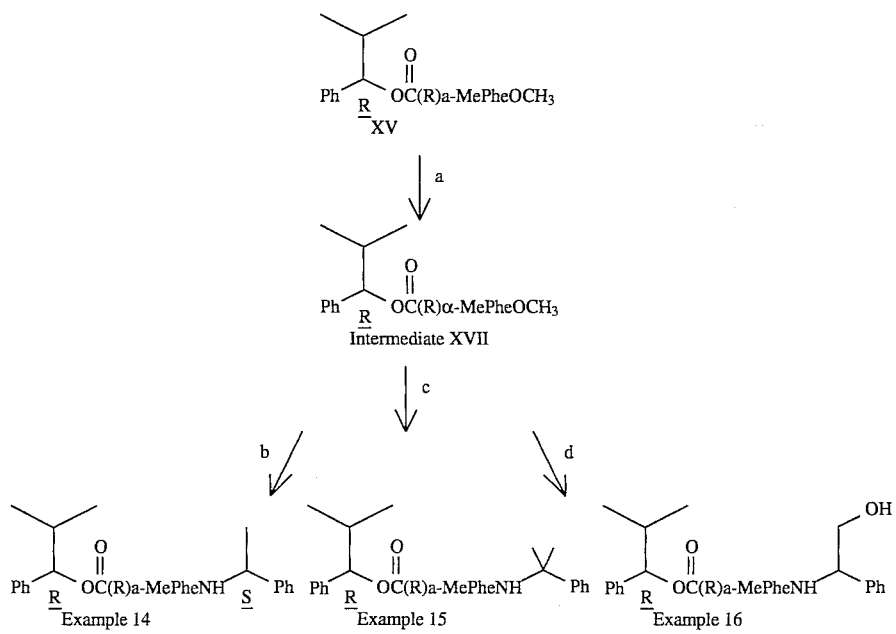

Reagents and conditions:
a) LiOH, THF:H$_2$O
b) DCCI, HOBT, (S)-α-methylbenzylamine, ETOAc
c) HBTU, DIPEA, cumylamine, DMF
d) HBTU, DIPEA, (R)-2-phenylglycinol, DMF In Scheme 11, Intermediate XV is hydrolyzed under basic conditions to give the carboxylic acid which is coupled using active ester methodology with (S)-α-methylbenzylamine, cumylamine, and (R)-2-phenylglycinol to yield Examples 14, 15, and 16, respectively.

Step 1 p-Toluenesulfonic acid (0.10 g, 0.53 mmol) was added to a solution of 8-bromoactanoic acid (35.15 g, 156 mmol) in MeOH (100 mL) and the mixture heated at reflux for 2.5 hours. After cooling, the solvent was removed in vacuo and

SCHEME 12

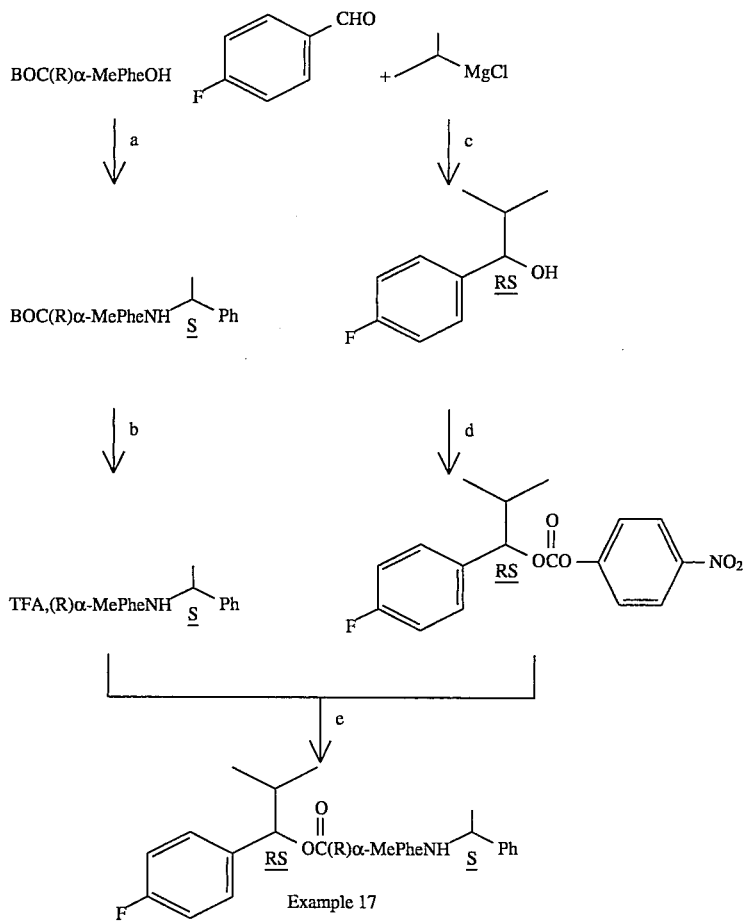

Example 17

Reagents and conditions:
a) DCCI, HOBT, (S)-α-methylbenzylamine, EtOAc
b) TFA, DCM
c) Et$_2$O
d) 4-nitrophenylchloroformate, Py, DCM
e) DMAP, DMF Scheme 12 describes the preparation of Example 17 BOC (R)-α-MePhe-OH is converted to the (S)-α-methylbenzylamine by active ester coupling. Acid catalyzed removal of the BOC group gives the amine salt. Base promoted coupling to the carbonate derived from the product of the Grignard reaction between 4-fluorobenzaldehyde and isopropyl magnesium chloride yields Example 17.

The following nonlimiting examples illustrate he methods for preparing the compounds of the invention.

SYNTHESIS OF INTERMEDIATE I

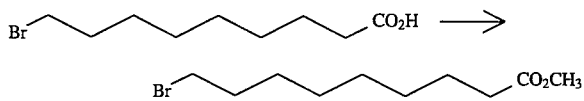

the residue dissolved in Et$_2$O (250 mL) and washed with saturated NaHCO$_3$ (2×100 mL) and one with brine (100 mL). The Et$_2$O layer was separated and dried over MgSO$_4$ and the solvent removed in vacuo giving the product as a mobile yellow liquid (37 g, 100%). This product was used directly without any further purification.

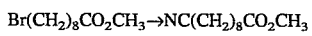

Step 2

Sodium cyanide (8.10 g, 165 mmol) was added to a solution of the bromo ester (37.3 g, 157 mmol) in DMSO (100 mL) and the mixture heated to 90° C. for 2 hours. The mixture was allowed to cool and the solid mass broken up and poured into water (600 mL) containing saturated NaHCO$_3$ (50 mL). The solution was extracted with Et$_2$O (2×300 mL) and the combined extracts washed with water and brine. The Et$_2$O was dried over MgSO$_4$, filtered, and the solvent removed in vacuo giving the product as a pale orange liquid (26.9 g, 93%).

IR (film: 2936, 2860, 2246, 1739, 1437, 1363, 1199, 1101, and 1017 cm$^{-1}$.

δ NMR (CDCl$_3$): 1.30–1.68 (10H, m, 5C$\underline{H}_2$), 2.29–2.36 (4H, m, 2C$\underline{H}_2$), and 3.67 (3H, s, CCOC$\underline{H}_3$).

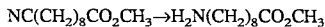

Step 3

The cyano ester (14.36 g, 79.45 mmol) was dissolved in 5% NH$_3$/MeOH (100 mL) and hydrogenated over Ra—Ni (25 mL) at 50 psi and 30° C. for 6 hours. The catalyst was filtered off and the solids washed well with methanol. The solvent was removed in vacuo giving the product as a waxy solid (13.80 g, 93%). This product was used without further purification.

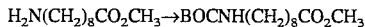

Step 4

A solution of di-tert-butyldicarbonate (17.69 g, 81.1 mmol) in DMF (50 mL) was added dropwise over 10 minutes to a stirred solution of the amino ester (13.80 g, 73.7 mmol) and DMAP (0.53 g, 4.34 mmol) in DMF (100 mL). The mixture was stirred for 1 hour at room temperature and then the solvent was removed in vacuo. The residue was dissolved in Et$_2$O and washed with water. The aqueous solution was extracted once more with Et$_2$O and the combined Et$_2$O extracts washed once with 10% citric acid, once with water, and once with brine. The Et$_2$O solution was dried over MgSO$_4$, filtered, and the solvent removed in vacuo. Purification of the residue by chromatography on silica using 33% EtOAc:67% n-hexane as eluant gave the product as a gum (8.82 g, 42%).

IR (film): 3378, 2976, 2931, 2857, 1740, 1716, 1520, 1366, 1250, and 1174 cm$^{-1}$.

δ NMR (CDCl$_3$): 1.30–1.63 (21H, m, (C$\underline{H}_3$)$_3$C, 6C$\underline{H}_2$), 2.30 (2H, t, J=7.6 Hz, C$\underline{H}_2$CO$_2$CH$_3$), 3.07–3.13 (2H, m, NHC$\underline{H}_2$), 3.67 (3H, s, CO$_2$C$\underline{H}_3$), and 4.55 (1H, b, OCON$\underline{H}$).

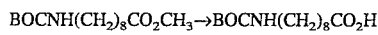

Step 5

LiOH.H$_2$O (3.78 g, 90 mmol) was added to a stirred solution of the ester (7.14 g, 24.7 mmol) in THF:H$_2$O (50 mL, 4:1 mixture) and the mixture stirred overnight at room temperature. The solvent was removed in vacuo and the residue dissolved in water and washed once with Et$_2$O. The aqueous layer was separated and made pH 2 with citric acid solution and extracted with EtOAc (×2). The combined extracts were washed with water and brine, dried over MgSO$_4$, filtered, and the solvent removed in vacuo. This gave the product as an oil which crystallized to a waxy solid on cooling (6.72 g, 99%).

δ NMR (DMSO-d$_6$): 1.19–1.45 (21H, m, (C$\underline{H}_3$)$_3$C, 6C$\underline{H}_2$), 2.14 (2H, t, J=7.2 Hz, C$\underline{H}_2$COOH), 2.81–2.86 (2H, m, NHC$\underline{H}_2$), 6.69 (1H, b, OCON$\underline{H}$), and 11.90 (1H, s, COO$\underline{H}$).

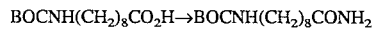

Step 6

Pentafluorophenol (0.502 g, 2.73 mmol) and N,N$^1$-dicyclohexylcarbodiimide (0.564 g, 2.74 mmol) were added to a stirred solution of the acid (0.789 g, 2.89 mmol) in CH$_2$Cl$_2$ (6 mL). The mixture was stirred for 2 hours at room temperature and the N,N$^1$-dicyclohexyl urea filtered off.

Ammonia gas was bubbled through the solution for 10 minutes giving a suspension which was dissolved in CHCl$_3$. The CHCl$_3$ solution was washed with K$_2$CO$_3$ solution and the aqueous layer separated and re-extracted with CHCl$_3$. The combined extracts were washed once with K$_2$CO$_3$ solution and once with brine, dried over MgSO$_4$, filtered, and the solvent removed in vacuo giving the product as a white solid (0.516 g, 69%).

IR (film): 3363, 2924, 2850, 1684, 1651, 1633, 1525, 1471, 1411, 1365, 1318, and 1251 cm$^{-1}$.

δ NMR (CDCl$_3$): 1.31–1.65 (12H, m, 6C$\underline{H}_2$), 1.44 (9H, s, (C$\underline{H}_3$)$_3$C), 2.22 (2H, t, J=7.6 Hz, C$\underline{H}_2$CONH$_2$), 3.09–3.11 (2H, m, C$\underline{H}_2$NHCOO), 4.51 (1H, b, OCON$\underline{H}$), 5.37 (1H, b, CON$\underline{HH}$), and 5.48 (1H, b, CONH$\underline{H}$).

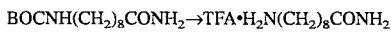

Step 7

The amide (5.63 g, 20.6 mmol) was dissolved in TFA:CH$_2$Cl$_2$ (40 mL, 1:1 mixture) and stirred for 2 hours at room temperature. The solvent was removed in vacuo giving the product as a gum which was used without further purification.

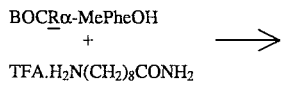

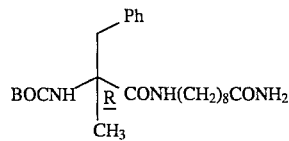

Step 8

HBTU (7.83 g, 20.65 mmol) was added to a stirred solution of the acid (5.77 g, 20.60 mmol) in anhydrous DMF (30 mL) at 0° C. Diisopropylethylamine (7.17 mL, 41.2 mmol) was added dropwise and the mixture stirred for 20 minutes at 0° C. This was followed by a solution of the aminoamide TFA salt (5.9 g, 20.6 mmol) and diisopropylethylamine (7.17 mL, 41.2 mmol) in DMF (30 mL) added dropwise over 30 minutes and at 0° C. The cold mixture was stirred with slow rewarming to room temperature for 2.5 hours and the solvent removed in vacuo. The residue was dissolved in EtOAc and washed with 10% citric acid solution (×2), saturated NaHCO$_3$ solution (×2), and once with brine. The EtOAc was dried over MgSO$_4$, filtered, and the solvent removed in vacuo. Purification of the residue by chromatography on silica using 5% MeOH:95% CH$_2$Cl$_2$ as eluant gave the product as a white solid (4.11 g, 46%).

IR (film): 3332, 3225, 2929, 2856, 1712, 1653, 1542, 1495, 1366, 1250, 1165, and 1077 cm$^{-1}$.

δ NMR (CDCl$_3$): 1.31–1.66 (15H, m, αC$\underline{H}_3$, 6C$\underline{H}_2$), 1.47 (9H, s, (C$\underline{H}_3$)$_3$C), 2.22 (2H, t, J=7.2 Hz, C$\underline{H}_2$CONH$_2$), 3.07 (1H, d, J=13.6 Hz, PhC$\underline{H}$H), 3.21–3.27 (2H, m, CONHC$\underline{H}_2$), 3.38 (1H, d, J=13.6 Hz, PhCH$\underline{H}$), 4.79 (1H, s, OCON$\underline{H}$), 5.30 (1H, b, CON$\underline{H}$H), 5.55 (1H, b, CONH$\underline{H}$), 6.32 (1H, b, CON$\underline{H}$CH$_2$), 7.12–7.15 (2H, m, aromatic), and 7.23–7.31 (3H, m, aromatic).

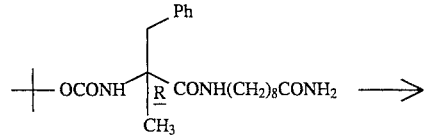

-continued

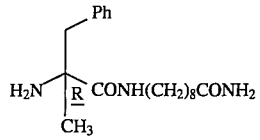

Step 9

The protected aminoamide (4.08 g, 9.41 mmol) was dissolved in a mixture of TFA (10 mL) and $CH_2Cl_2$ (10 mL) and stirred for 1 hour at room temperature. The solvent was removed in vacuo and the residue dissolved in EtOAc (100 mL) and washed with $K_2CO_3$ solution (2×50 mL). The aqueous solution was re-extracted with EtOAc (2×50 mL) and the combined EtOAc extracts washed with water (50 mL) and brine (50 mL). The EtOAc was dried over $MgSO_4$, filtered, and the solvent removed in vacuo to give the product as a white solid (3.27 g, 100%), mp 81°–82° C.

$[\alpha]_D^{20}$ +60.8° (C=1.0, $CHCl_3$).

IR (film): 3352, 3195, 2928, 2855, 1652, 1524, 1454, 1406, and 1125 $cm^{-1}$.

δ NMR ($CDCl_3$): 1.22–1.43 (10H, m, 5C$\underline{H}_2$), 1.62–1.65 (2H, m, CONHCH$_2$C$\underline{H}_2$), 2.22 (2H, t, J=8.0 Hz, C$\underline{H}_2$CONH$_2$), 2.62 (1H, d, J=13.2 Hz, PhC$\underline{H}$H), 3.15–3.18 (2H, m, CONHC$\underline{H}_2$), 3.38 (1H, d, J=13.2 Hz, PhCH$\underline{H}$), 5.53 (1H, b, CON$\underline{H}$H), 5.65 (1H, b, CONH$\underline{H}$), 7.16–7.28 (5H, m, $C_6\underline{H}_5$), and 7.47 (1H, b, CON$\underline{H}$CH$_2$).

Analysis calculated for $C_{19}H_{31}N_3O_2$·0.15 $H_2O$: C, 67.88; H, 9.38; N, 12.50. Found: C, 67.86; H, 9.30; N, 12.41.

SYNTHESIS OF EXAMPLE 1

Carbamic acid, [2-[(9-amino-9-oxononyl)amino]-1-methyl-2-oxo-1-(phenylmethyl)ethyl]-, 2-methyl-1-phenylpropyl ester, [R-(R*,S*)]–

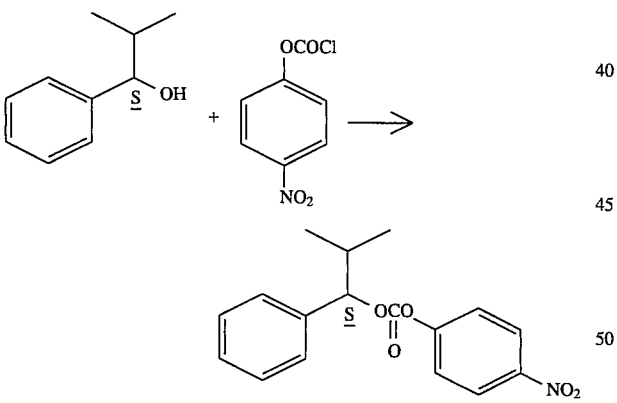

Step 1

A solution of triethylamine (0.550 mL, 4.0 mmol) in anhydrous THF (10 mL) was added dropwise over 10 minutes to a stirred solution of p-nitrophenyl-chloroformate (0.671 g, 3.33 mmol) and S-(−)-2-methyl-1-phenyl-1-propanol (0.500 g, 3.33 mmol) in anhydrous THF (10 mL) cooled to 5° C. The cooled solution was stirred with slow rewarming to room temperature over 48 hours and then $Et_2O$ (100 mL) was added. The mixture was washed with 5% citric acid solution (2×25 mL) and once with brine (25 mL). The $Et_2O$ solution was dried over $MgSO_4$, filtered, and the solvent removed in vacuo. Purification of the residue by chromatography on silica using 10% $Et_2O$:90% n-hexane as eluant gave the product as a gum (0.335 g, 32%).

IR (film): 3362, 1764, 1526, 1254, and 1218 $cm^{-1}$.

δ NMR ($CDCl_3$): 0.85 (3H, d, J=6.8 Hz, C$\underline{H}_3$CHCH$_3$), 1.09 (3H, d, J=6.8 Hz, CH$_3$CHC$\underline{H}_3$), 2.22–2.27 (1H, m, CH$_3$C$\underline{H}$CH$_3$), 5.38 (1H, d, J=7.6 Hz, PhC$\underline{H}$), 7.26–7.41 (7H, m, aromatic), and 8.24 (2H, d, J=9.2 Hz, aromatic).

Analysis calculated for $C_{17}H_{17}NO_5$: C, 64.75; H, 5.44; N, 4.44: Found: C, 64.89; H, 5.46; N, 4.39.

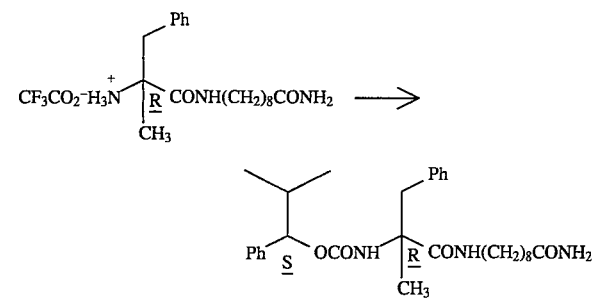

Step 2

DMAP (0.010 g, 0.08 mmol) was added to a stirred solution of the amine salt (0.117 g, 0.262 mmol) (Intermediate I), carbonate (0.091 g, 0.288 mmol) (Intermediate II), and triethylamine (0.040 mL, 0.288 mmol) in anhydrous DMF (5 mL) at room temperature. The solution was stirred at room temperature for 30 hours and then diluted with EtOAc (50 mL). The EtOAc solution was washed with 10% citric acid solution (2×25 mL), 10% $K_2CO_3$ solution (4× 25 mL), 10% citric acid solution (25 mL), and once with brine (25 mL). The EtOAc was dried over $MgSO_4$, filtered, and the solvent removed in vacuo. Purification of the residue by chromatography on silica using EtOAc as eluant gave the product as a foam (0.013 g, 10%).

IR (film): 3338, 3211, 2929, 2855, 1712, 1655, 1495, and 1079 $cm^{-1}$.

δ NMR ($CDCl_3$): 0.80 (3H, d, J=6.8 Hz, C$\underline{H}_3$CHCH$_3$), 0.98 (3H, d, J=6.6 Hz, CH$_3$CHC$\underline{H}_3$), 1.24–1.46 (10H, m, 5C$\underline{H}_2$), 1.42 (3H, s, C$\underline{H}_3$), 1.60–1.76 (2H, m, C$\underline{H}_2$), 2.04–2.12 (1H, m, CH$_3$C$\underline{H}$CH$_3$), 2.22 (2H, t, J=7.3 Hz, C$\underline{H}_2$CONH$_2$), 3.09 (1H, d, J=13.7 Hz, PhCH$\underline{H}$), 3.14–3.25 (2H, m, CONHC$\underline{H}_2$), 3.32 (1H, d, J=13.9 Hz, PhC$\underline{H}$H), 5.16 (1H, b, OCON$\underline{H}$), 5.39 (1H, b, CONH$\underline{H}$), 5.39 (1H, d, J=7.8 Hz, PhC$\underline{H}$(O)CH), 5.55 (1H, b, CON$\underline{H}$H), 6.22 (1H, b, CON$\underline{H}$CH$_2$), 6.94–6.95 (2H, m, Ph), and 7.14–7.38 (8H, m, Ph).

HPLC: 93.3% pure.

SYNTHESIS OF EXAMPLE 2

Carbamic acid, [2-[(9-amino-9-oxononyl)amino]-1-methyl-2-oxo-1-(phenylmethyl)ethyl]-, 1-(4-chlorophenyl)-2-methylpropyl ester

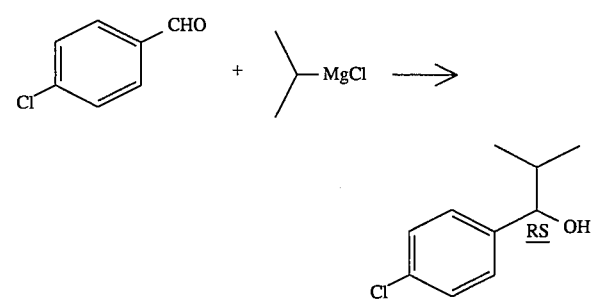

29

Step 1

Isopropyl magnesium chloride (6.0 mL, 2.0 mL solution in Et$_2$O, 12 mmol) was added dropwise over 5 minutes to a stirred solution of the aldehyde (1.24 g, 8.82 mmol) in anhydrous Et$_2$O (25 mL) cooled to 5° C. The mixture was stirred for 20 minutes at 5° C. and then at room temperature for 40 minutes. 1N HCl (25 mL) was added and the Et$_2$O layer separated. The aqueous solution was extracted with Et$_2$O (2×25 mL) and the combined Et$_2$O extracts dried over MgSO$_4$, filtered, and the solvent removed in vacuo. Purification of the residue by chromatography on silica using 30% Et$_2$O:70% n-hexane as eluant gave the product as a gum (1.19 g, 73%).

IR (film): 3384, 2961, 2873, 1490, 1090, and 1014 cm$^{-1}$.

δ NMR (CDCl$_3$): 0.80 (3H, d, J=6.8 Hz, CH$_3$CHCH$_3$), 0.97 (3H, d, J=6.4 Hz, CH$_3$CHCH$_3$), 1.86 (1H, s, OH), 1.88–1.96 (1H, m, CH$_3$CHCH$_3$), 4.35–4.37 (1H, m, PhCHOH), and 7.23–7.32 (4H, m, pCl C$_6$H$_4$).

Analysis calculated for C$_{10}$H$_{13}$ClO: C, 65.04; H, 7.10. Found: C, 64.75; H, 7.11.

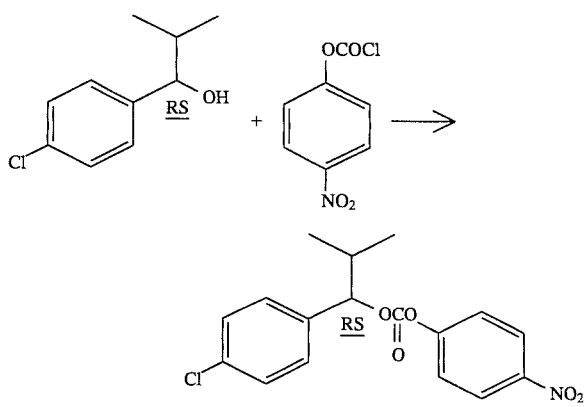

Step 2

A solution of triethylamine (0.83 mL, 5.95 mmol) in anhydrous THF (20 mL) was added dropwise over 20 minutes to a stirred solution of the alcohol (1.0 g, 5.41 mmol) and p-nitrophenylchloroformate (1.09 g, 5.41 mmol) in anhydrous THF (20 mL) cooled to 5° C. The mixture was stirred with slow rewarming to room temperature for 48 hours and then Et$_2$O (100 mL) was added. The solution was washed with 5% citric acid (2×25 mL) and once with brine (25 mL). The Et$_2$O solution was dried over MgSO$_4$, filtered, and the solvent removed in vacuo. Purification of the residue by chromatography on silica using 10% Et$_2$O:90% n-hexane as eluant gave the product as a gum (0.972 g, 51% ).

IR (film): 3356, 2968, 1764, 1526, 1492, 1347, 1254, and 1218 cm$^{-1}$.

δ NMR (CDCl$_3$): 0.85 (3H, d, J=6.8 Hz, CH$_3$CHCH$_3$), 1.09 (3H, d, J=6.4 Hz, CH$_3$CHCH$_3$), 2.18–2.24 (1H, m, CH$_3$CHCH$_3$), 5.33 (1H, d, J=8.0 Hz, PhCHO), 7.26–7.38 (6H, m, aromatic), and 8.25 (2H, d, J=8.8 Hz, aromatic).

Analysis calculated for C$_{17}$H$_{16}$ClNO$_5$: C, 58.38; H, 4.61; N, 4.01; Cl, 10.14. Found: C, 58.67; H, 4.70; N, 3.90; Cl, 10.49.

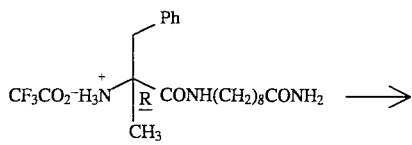

30

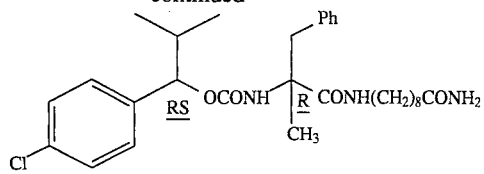

Step 3

DMAP (0.010 g, 0.08 mmol) was added to a stirred solution of the amine salt (0.156 g, 0.349 mmol) (Intermediate I), carbonate (0.134 g, 0.384 mmol) (Intermediate III), and triethylamine (0.054 mL, 0.384 mmol) in anhydrous DMF (5 mL) at room temperature. The solution was stirred at room temperature for 24 hours and then diluted with EtOAc (50 mL). The EtOAc solution was washed with 5% citric acid (2×25 mL), 10% K$_2$CO$_3$ (4×25 mL), 5% citric acid (25 mL), and once with brine (25 mL). The EtOAc was dried over MgSO$_4$, filtered, and the solvent removed in vacuo. Purification of the residue by chromatography on silica using EtOAc as eluant gave the product as a foam (0.037 g, 20%).

IR (film): 3338, 3208, 2930, 2856, 1716, 1654, 1492, 1077, and 733 cm$^{-1}$.

δ NMR (CDCl$_3$): 0.79–0.81 (3H, m, CH$_3$CHCH$_3$), 0.95–0.99 (3H, m, CH$_3$CHCH$_3$), 1.19–1.48 (12H, m, 6C H$_2$), 1.44 and 1.48 (3H, 2s, CH$_3$), 1.59–1.67 (2H, m, C H$_2$), 2.00–2.08 (1H, m, CH$_3$CHCH$_3$), 2.21 (2H, t, J=7.6 Hz, CH$_2$CONH$_2$), 3.10–3.31 (4H, m, CONHCH$_2$, PhCH$_2$), 5.32–5.36 (1H, m, pClC$_6$H$_4$CHO), 5.42 (1H, b, OCONH), 5.50 (1H, b, CONHH), 5.59 (1H, b, CONHH), 6.08 and 6.19 (1H, 2bs, CONH), 6.95–6.99 (2H, m, aromatic), and 7.16–7.34 (7H, m, aromatic).

HPLC: 97.8%.

Analysis calculated for C$_{30}$H$_{42}$ClN$_3$C$_4$.0.25 H$_2$O: C, 65.67; H, 7.81; N, 7.66; Cl, 6.46. Found: C, 65.46; H, 7.64; N, 7.52; Cl, 6.76.

SYNTHESIS OF EXAMPLE 3

[1-(8-Carbamoyl-octylcarbamoyl)-1-methyl-2-phenyl-ethyl]-carbamic acid cyclopentyl-phenyl-methyl ester

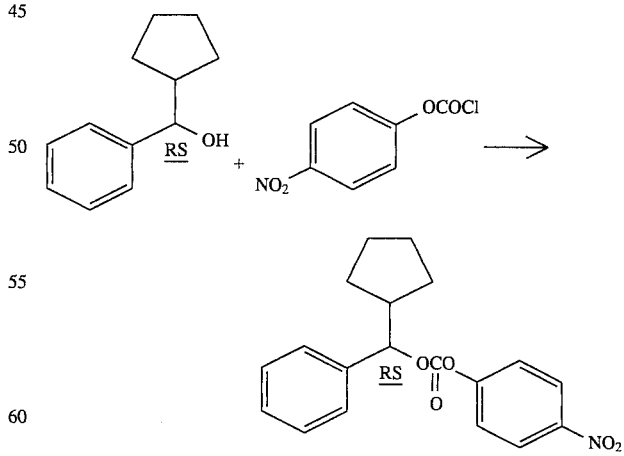

Step 1

A solution of triethylamine (1.67 mL, 12 mmol) in anhydrous THF (10 mL) was added dropwise over 10 minutes to a stirred solution of the alcohol (1.76 g, 10 mmol) and p-nitrophenylchloroformate (2.02 g, 10 mmol) in anhydrous THF (25 mL) cooled to 5° C. The cooled mixture was stirred with slow rewarming to room temperature for 24 hours and then Et$_2$O (100 mL) was added. The mixture was washed with 5% citric acid solution (2×25 mL), saturated NaHCO$_3$ (25 mL), and once with brine (25 mL). The Et$_2$O solution was dried over MgSO$_4$, filtered, and the solvent removed in vacuo. Purification of the residue by chromatography on silica using 10% Et$_2$O:90% n-hexane as eluant gave the product as a gum (2.03 g, 60%).

IR (film): 2957, 2870, 1763, 1525, and 1215 cm$^{-1}$.

δ NMR (CDCl$_3$): 1.12–1.25 (1H, m, cyclopentyl), 1.40–1.72 (6H, m, cyclopentyl), 1.91–1.99 (1H, m, cyclopentyl), 2.43–2.57 (1H, m, cyclopentyl), 5.44 (1H, d, J=9.3 Hz, CHOCO), 7.30–7.41 (7H, m, aromatic), and 8.23 (1H, d, J=9.2 Hz, aromatic).

Analysis calculated for C$_{19}$H$_{19}$NO$_5$: C, 66.85; H, 5.61; N, 4.10. Found: C, 66.95; H, 5.61; N, 4.07.

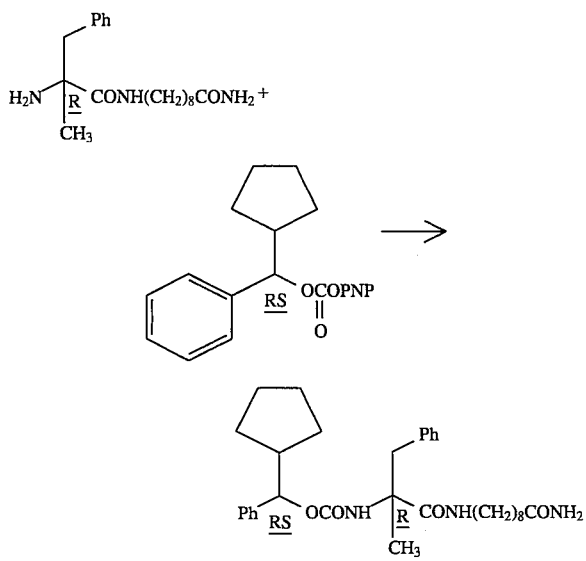

Step 2

DMAP (0.055 g, 0.450 mmol) was added to a stirred solution of the aminoamide (0.050 g, 0.150 mmol) (Intermediate I) and carbonate (0.154 g, 0.450 mmol) in anhydrous DMF (1 mL) at room temperature. The solution was stirred at room temperature for 48 hours and then diluted with EtOAc (50 mL). The EtOAc solution was washed with 10% citric acid solution (2×25 mL), 10% K$_2$CO$_3$ solution (4×25 mL), and once with brine (25 mL). The EtOAc was dried over MgSO$_4$, filtered, and the solvent removed in vacuo. Purification of the residue by chromatography on silica using 50% EtOAc:50% n-hexane as eluant gave the product as a white solid (0.048 g, 60%), mp 45°–50° C.

IR (film): 3339, 3209, 3063, 3031, 2932, 2858, 1711, 1655, 1488, 1078, and 733 cm$^{-1}$.

δ NMR (CDCl$_3$): 1.10–1.83 (20H, m, 6CH$_2$, cyclopentyl), 1.39 and 1.45 (3H, 2s, CH$_3$), 2.21 (2H, t, J=7.6 Hz, CH$_2$CONH$_2$), 2.32–2.37 (1H, m, cyclopentylCH), 3.06–3.35 (4H, m, PhCH$_2$, CONHCH$_2$), 5.12 and 5.26 (1H, 2bs, OCONH), 5.42–5.46 (1H, m, PhCHOCO), 5.52 (1H, b, CONHH), 5.64 (1H, b, CONHH), 6.11 and 6.27 (1H, 2bs, CONHCH$_2$), 6.93–7.00 (2H, m, aromatic), and 7.14–7.38 (8H, m, aromatic).

HPLC: 100% pure.

Analysis calculated for C$_{32}$H$_{45}$N$_3$O$_4$·0.25 H$_2$O: C, 71.14; H, 8.49; N, 7.78. Found: C, 70.78; H, 8.39; N, 7.53.

SYNTHESIS OF EXAMPLE 4

[1-(8-Carbamoyl-octylcarbamoyl)-1-methyl-2-phenyl-ethyl]-carbamic acid 2,2-dimethyl-1,2,3,4-tetrahydro-naphthalen-1-yl ester

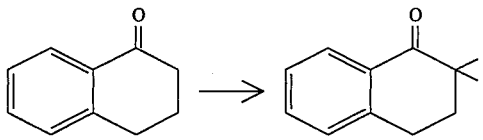

Step 1

α-Tetralone (0.66 mL, 5.0 mmol) in anhydrous THF (2 mL) was added to a stirred suspension of sodium hydride (0.40 g, 60% dispersion in mineral oil, 10 mmol) in anhydrous THF (20 mL) under a N$_2$ atm at room temperature. To this mixture was added methyl iodide (0.62 mL, 10 mmol) and the mixture heated at reflux for 5 hours. After cooling, EtOAc (2 mL) was added carefully and then the solvent removed in vacuo. The residue was taken up in EtOAc (60 mL) and washed with water (3×50 mL), the EtOAc extract dried over MgSO$_4$, filtered, and the solvent removed in vacuo. Purification of the residue by chromatography on silica using n-hexane and then 2% Et$_2$O:98% n-hexane as eluant gave the product as a colorless oil (0.57 g, 65%).

IR (film): 2963, 2927, 1684, and 1603 cm$^{-1}$.

δ NMR (CDCl$_3$): 1.22 (6H, s, 2CH$_3$), 1.99 (2H, t, J=6.0 Hz, CH$_2$), 2.99 (2H, t, J=6.4 Hz, CH$_2$), and 7.20–8.04 (4H, m, aromatic).

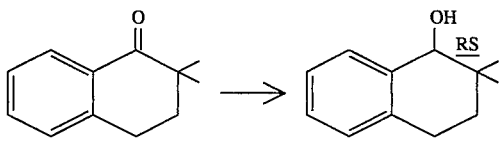

Step 2

Sodium borohydride (0.056 g, 1.50 mmol) was added in portions to a stirred solution of the ketone (0.54 g, 3.1 mmol) in anhydrous MeOH (12 mL) at 0° C. After stirring for 30 minutes, a further portion of sodium borohydride (0.050 g, 1.3 mmol) was added and the mixture stirred for 1 hour at room temperature. 2N HCl (4 mL) was added dropwise and the solvent removed in vacuo. 2N HCl (30 mL) was added to the residue and the mixture extracted with EtOAc (3×60 mL). The combined EtOAc extracts were dried over MgSO$_4$, filtered, and the solvent removed in vacuo. Purification of the residue of chromatography on silica using 20% Et$_2$O:80% n-hexane as eluant gave the product as a colorless oil (0.26 g, 48%).

δ NMR (CDCl$_3$): 0.99 (3H, s, CH$_3$), 1.01 (3H, s, CH$_3$), 1.50–1.60 (1H, m, CHH), 1.80 (1H, m, CHH), 2.72–2.90 (2H, m, CH$_2$), 4.27 (1H, s, CHOH), and 7.08–7.50 (4H, m, aromatic).

m$^+$ 159 (100%), 177 (m+1).

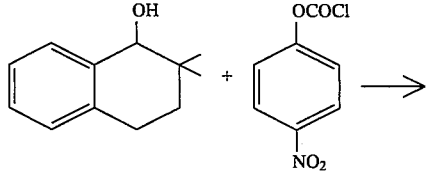

-continued

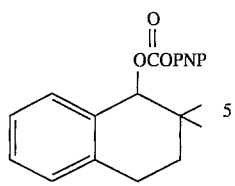

Step 3

A solution of p-nitrophenylchloroformate (0.286 g, 1.42 mmol) in EtOAc (3 mL) was added dropwise at room temperature to a stirred solution of the alcohol (0.25 9, 1.42 mmol) and pyridine (0.115 mL, 1.42 mmol) in EtOAc (12 mL). After stirring for 18 hours, the mixture was filtered and the solvent removed in vacuo. Purification of the residue by chromatography on silica using 10% $Et_2O$:90% n-hexane as eluant gave the product (Intermediate V) as a yellow oil (0,085 g, 18%).

δ NMR ($CDCl_3$): 0.99 (3H, s, $CH_3$), 1.15 (3H, s, $CH_3$), 1.52–1.64 (1H, m, $CH_2$), 1.95–2.04 (1H, m, $CH_2$), 2.80–3.00 (2H, m, $CH_2$), 5.58 (1H, s, CHOH), 7.15–7.40 (6H, m, aromatic), and 8.25–8.34 (2H, m, aromatic).

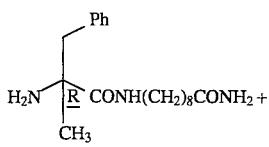

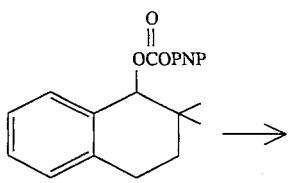

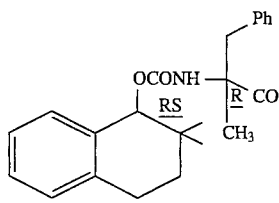

Step 4

DMAP (0.027 g, 0.225 mmol) was added to a stirred solution of the aminoamide (0.075 g, 0.225 mmol) (Intermediate I) and carbonate (0.073 g, 0.225 mmol) (Intermediate V) in anhydrous DMF (5 mL) at room temperature. The mixture was stirred at room temperature for 10 days and then diluted with EtOAc (50 mL). The EtOAc solution was washed with 2N HCl (2×30 mL) and 10% $Na_2CO_3$ solution (4×50 mL), the EtOAc dried over $MgSO_4$, filtered, and the solvent removed in vacuo. Purification of the residue by chromatography on silica using 40% EtOAc:60% n-hexane, EtOAc, and then 5% MeOH:95% EtOAc as eluant gave the product as an off-white solid (0.015 g, 12%).

IR (film): 3339, 2926, 1708, and 1653 $cm^{-1}$.

δ NMR ($CDCl_3$): 0.94–1.94 (23H, m, $2CH_3$, α$CH_3$, 6C$H_2$, $CH_2C(CH_3)_2$), 2.22 (2H, t, J=8 Hz, $CH_2CONH_2$), 2.75–3.45 (6H, m, $CH_2$Ph, $CH_2$Ph, $NHCH_2$), 5.00 and 5.03 (1H, 2s, OCONH), 5.25 and 5.50 (1H, 2bs, CONHH), 5.60 (1H, s, CHOCO), 6.18 and 6.25 (1H, 2bs, CONHH), and 7.00–7.40 (10H, m, CONHCH$_2$, aromatic).

HPLC: 97% pure.

m$^+$ 536 (m+1), 447, 334.

SYNTHESIS OF EXAMPLE 5

[1-(8-Carbamoyl-octylcarbamoyl)-1-methyl-2-phenyl-ethyl]-carbamic acid 6,7,8,9-tetrahydro-5H-benzocyclohepten- 5-yl ester

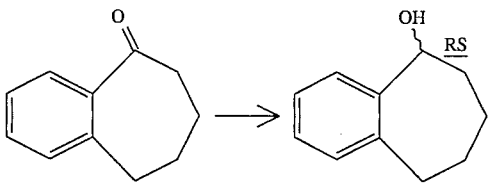

Step 1

Sodium borohydride (0.594 g, 15.71 mmol) was added in portions over 10 minutes to a stirred solution of 1-benzosuberone (1.007 g, 6.29 mmol) in isopropanol (25 mL) cooled to 5° C. The cooled mixture was stirred with slow rewarming to room temperature over 2.5 hours. The solution was re-cooled to 5° C. and 1N HCl (50 mL) was added dropwise over 1 hour. The isopropanol was evaporated and the residual mixture extracted with EtOAc (3×50 mL). The combined extracts were dried over $MgSO_4$, filtered, and the solvent removed in vacuo. Purification of the residue by chromatography on silica using 75% n-hexane:25% EtOAc as eluant gave the product as a white solid (0.84 g, 82%), mp 98°–100° C.

IR (film): 3189, 2924, 2847, 1446, 1044, 759, and 733 $cm^{-1}$.

δ NMR ($CDCl_3$): 1.44–2.09 (7H, m, $3CH_2$, OH), 2.68–2.75 (1H, m, PhCHHCH$_2$), 2.93 (1H, dd, J=14.2 Hz, 8.3 Hz, PhCHHCH$_2$), 4.94 (1H, d, J=7.6 Hz, CHOH), 7.08–7.23 (3H, m, aromatic), and 7.44 (1H, d, J=7.3 Hz, aromatic).

Analysis calculated for $C_{11}H_{14}O$: C, 81.44; H, 8.70. Found: C, 81.53; H, 8.86.

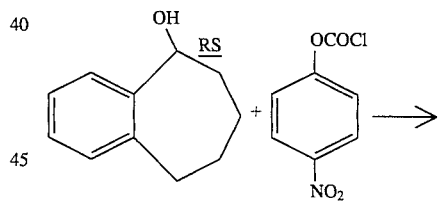

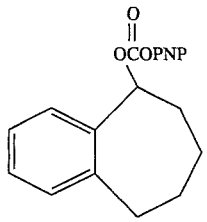

Step 2

A solution of pyridine (0.299 mL, 3.70 mmol) in EtOAc (10 mL) was added dropwise over 45 minutes to a stirred solution of the alcohol (0.50 g, 3.08 mmol) and p-nitrophenylchloroformate (0.745 g, 3.70 mmol) in EtOAc (10 mL) cooled to 5° C. The cooled mixture was stirred with slow rewarming to room temperature over 2 hours and then washed with 10% citric acid (2×20 mL) and once with brine (20 mL). The EtOAc was dried over $MgSO_4$, filtered, and the solvent removed in vacuo. Purification of the residue by chromatography on silica using 10% $Et_2O$:90% n-hexane as eluant gave the product (Intermediate VII) as a white solid (0.583 g, 58%), mp 78°–82° C.

IR (film): 3387, 2931, 2855, 1762, 1616, 1594, 1524, 1492, 1346, 1260, 1212, and 859 cm$^{-1}$.

δ NMR (CDCl$_3$): 1.68–1.74 (2H, m, C$\underline{H}_2$), 1.86–2.19 (4H, m, 2C$\underline{H}_2$), 2.73–2.80 (1H, m, PhCH$\underline{H}$), 3.01–3.08 (1H, m, PhC$\underline{H}$H), 5.90 (1H, d, J=8.5 Hz, PhC$\underline{H}$OCO), 7.14–7.26 (3H, m, aromatic), 7.32–7.40 (3H, m, aromatic), and 8.27 (2H, d, J=9.0 Hz, aromatic).

Analysis calculated for C$_{18}$H$_{17}$NO$_5$: C, 66.05; H, 5.24; N, 4.28. Found: C, 66.13; H, 5.21; N, 4.29.

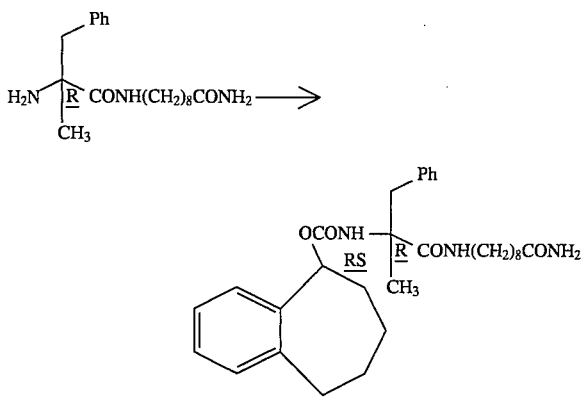

Step 3

DMAP (0.028 g, 0.229 mmol) was added to a stirred solution of the carbonate (0.225 g, 0.687 mmol) (Intermediate VII) and aminoamide (0.076 g, 0.229 mmol) (Intermediate I) in anhydrous DMF (2 mL) at room temperature. The solution was stirred at room temperature for 4 days and then diluted with EtOAc (50 mL). The EtOAc solution was washed with 10% citric acid (25 mL), 10% K$_2$CO$_3$ (6×25 mL), and once with brine (25 mL). The EtOAc was dried over MgSO$_4$, filtered, and the solvent removed in vacuo. Purification of the residue by chromatography on silica using EtOAc as eluant gave the product as a white foam (0.073 g, 61%), mp 57°–64° C.

IR (film): 3338, 2928, 2855, 1708, 1655, 1489, 1453, 1262, 1078, and 733 cm$^{-1}$.

δ NMR (CDCl$_3$): 1.25–2.05 (18H, m, 9C$\underline{H}_2$), 1.46 and 1.52 (3H, 2s, C$\underline{H}_3$), 2.21 (2H, t, J=7.3 Hz, C$\underline{H}_2$CONH$_2$), 2.72–2.78 (1H, m, PhCH$\underline{H}$), 2.91–2.96 (1H, m, PhC$\underline{H}$H), 3.11–3.38 (4H, m, CONHC$\underline{H}_2$, PhC$\underline{H}_2$), 5.22 (1H, b, OCON$\underline{H}$), 5.34 (1H, b, CONH$\underline{H}$), 5.51 (1H, b, CON$\underline{H}$H), 5.88–5.90 (1H, m, PhC$\underline{H}$O), 6.14 and 6.22 (1H, 2bs, CON$\underline{H}$CH$_2$), and 7.01–7.32 (9H, m, aromatic).

HPLC: 100% pure.

Analysis calculated for C$_{31}$H$_{43}$N$_3$O$_4$·0.25 H$_2$O: C, 70.76; H, 8.33; N, 7.99. Found: C, 70.55; H, 8.23; N, 7.84.

SYNTHESIS OF EXAMPLE 6

[1-(8-Carbamoyl-octylcarbamoyl)-1-methyl-2-phenyl-ethyl]-carbamic acid 6,6-dimethyl-6,7,8,9-tetrahydro-5H-benzocyclohepten-5-yl ester

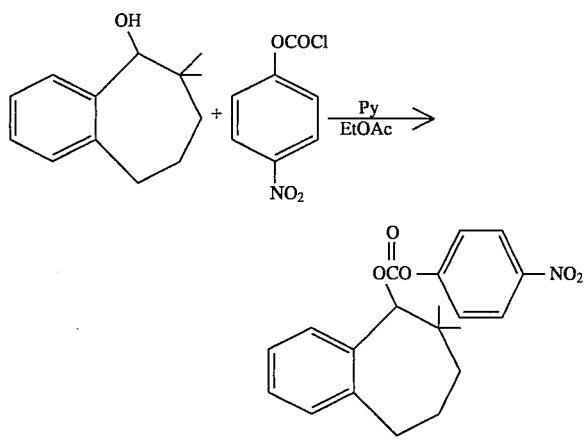

Step 1

Pyridine (0.203 mL, 2.52 mmol) in ethyl acetate (25 mL) was added dropwise over 1.5 hours to a solution of the alcohol (0.400 g, 2.10 mmol) and p-nitrophenyl-chloroformate (0.509 g, 2.52 mmol) in ethyl acetate (25 mL) cooled in an ice-water bath. The mixture was slowly warmed to room temperature and stirred for 24 hours. Additional p-nitrophenylchloroformate (0.25 mg, 1.26 mmol) was added and stirring continued for 20 hours.

The reaction mixture was washed with 1N HCl (2×25 mL) and brine (25 mL). Drying (MgSO$_4$) and further purification by column chromatography on silica, eluting with 10% diethyl ether:n-heptane yielded the carbonate (0.310 g, 42%) as a white solid.

IR (film): 2959, 2931, 2860, 1764, 1525, 1347, and 1554 cm$^{-1}$.

$^1$H NMR (CDCl$_3$): δ0.84 (3H, s, C$\underline{H}_3$), 1.09 (3H, s, —C$\underline{H}_3$), 1.55–1.80 (3H, m, C$\underline{H}_2$, CH$_2$C$\underline{H}$), 2.02–2.15 (1H, m, CH$_2$C$\underline{H}$), 2.63–2.70 (1H, m, ArCH$\underline{H}$), 3.04–3.13 (1H, m, ArC$\underline{H}$H), 5.45 (1H, s, PhC$\underline{H}$OCO), 7.11–7.25 (4H, m, Ar), 7.34 (2H, d, J=9.2 Hz, Ar), and 8.24 (2H, d, J=9.2 Hz, Ar).

m$^+$ 227, 185, 174, 173, and 117.

Analysis calculated for C$_{20}$H$_{20}$NO$_5$: C, 67.78; H, 5.69; N, 3.95. Found: C, 67.67; H, 5.96; N, 3.93.

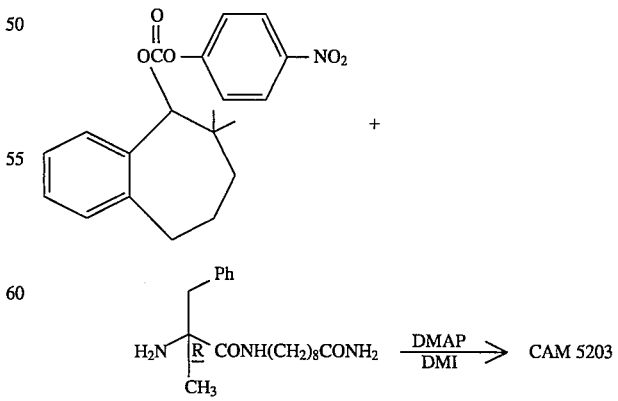

Step 2

DMAP (0.026 g, 0.22 mmol) was added to a stirred solution of the aminoamide (0.072 g, 0.22 mmol) (Intermediate I) and the carbonate (0.151 g, 0.43 mmol) (Intermediate VI) in anhydrous DMF (2 ML) and stirred at room temperature for 2 days.

The reaction mixture was diluted with ethyl acetate (50 mL) and washed with 10% potassium carbonate solution (5×25 mL) and brine (25 mL). Drying (MgSO$_4$) and further purification by column chromatography on silica, eluting with 50% ethyl acetate 50%:n-heptane and then ethyl acetate yielded the product (0.038 g, 31%).

IR (film): 3326, 2929, 2856, 1712, 1652, 1487, 1261, and 1098 cm$^{-1}$.

$^1$H NMR (CDCl$_3$): δ0.81 (3H, s, CH$_3$), 0.97 (3H, s, CH$_3$), 1.24–1.67 (18H, m, 6C$\underline{H}_2$, CH$\underline{H}$CH$_2$, C$\underline{H}$ $_2$CH$_2$, C$\underline{H}_3$), 1.92–1.98 (1H, m, CH$\underline{H}$CH$_2$), 2.22 (2H, t, J=7.3 Hz, CH$_2$CONH$_2$), 2.62–2.65 (1H, m, PhC$\underline{HH}$), 2.94–2.97 (1H, m, PhC$\underline{HH}$), 3.09 (1H, d, J=13.7 Hz, PhC$\underline{HH}$), 3.18–3.25 (2H, m, CONHC$\underline{H}_2$), 3.34 (1H, d, J=13.7 Hz, PhC$\underline{HH}$), 5.08 and 5.27 (1H, 2s, OCON$\underline{H}$), 5.27 (1H, b, CONH$\underline{H}$), 5.50 (1H, b, CONH$\underline{H}$), 5.50 (1H, s, PhC$\underline{H}$OCO), 6.01 and 6.23 (1H, 2s, CON$\underline{H}$CH$_2$), 6.88–6.96 (2H, m, Ar), and 7.06–7.28 (7H, m, Ar).

HPLC: 100%.

Analysis calculated for C$_{33}$H$_{47}$N$_3$O$_4$·0.4 H$_2$O: C, 71.16; H, 8.65; N, 7.55. Found: C, 71.32; H, 8.65; N, 7.47.

EXAMPLE 7

[1-Methyl-2-phenyl-1-(7-ureido-heptylcarbamoyl)-ethyl]-carbamic acid 2-methyl-1-phenyl-propyl ester

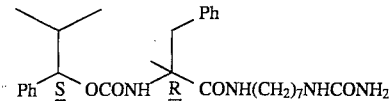

Step 1

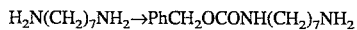

1,7-Heptanediamine (2.11 g, 16.2 mmol) was dissolved in 1,4-dioxane (2 L). To this solution was added water (200 mL) and Na$_2$CO$_3$·10 H$_2$O (6.96 g, 24.3 mmol). The solution was cooled in an ice bath and benzylchloroformate (2.3 mL, 16.1 mmol) in 1,4-dioxane (100 mL) was added dropwise over 6.5 hours. The resulting cold mixture was stirred with slow warming to room temperature for 17 hours. The 1,4-dioxane was removed in vacuo and the residue was dissolved in EtOAc (200 mL). The organic was washed with brine (3×50 mL), then dried over MgSO$_4$. Removal of the solvent in vacuo gave a solid 3.88 g (91%).

IR (film): 3347, 2928, 2855, 1687, 1652, 1532, and 1254 cm$^{-1}$.

Step 2

A solution of trimethylsilylisocyanate (2.2 mL, 16.2 mmol) in anhydrous THF (50 mL) was added dropwise over 1 hour to a stirred solution of the amine (3.88 g, 14.7 mmol) in anhydrous THF (50 mL). The resulting mixture was stirred for 18 hours and the solvent was then removed in vacuo. The residue was dissolved in EtOAc (100 mL) and washed with brine (2×50 mL), then dried over MgSO$_4$. The solvent was removed in vacuo and the residue was recrystallized from EtOAc to give a white solid 350 mg (8%).

IR (film): 3414, 3328, 2921, 2825, 1686, 1647, 1602, 1532, 1454, 1249, and 732 cm$^{-1}$.

NMR (CDCl$_3$): 1.17–1.39 (10H, m, 5×CH$_2$), 2.90–3.00 (4H, m, 2×CH$_2$), 5.00 (2H, s, PhC$\underline{H}_2$O), 5.32 (2H, s, CONH$_2$), 5.87 (1H, b, OCON$\underline{H}$), 7.22 (1H, br, $\underline{NH}$CONH$_2$), and 7.29–7.38 (5H, m, C$_6$H$_5$).

Step 3

The urea (343 mg, 1.1 mmol) was hydrogenated in EtOH (75 mL) over Pearlman's catalyst (34 mg) at 45 psi H$_2$ and 30° C. for 18 hours. The catalyst was removed by filtration and the solvent was removed in vacuo to give an off-white solid 163 mg (83%).

IR (film): 3339, 2930, 2857, 1649, 1567, 1489, and 1344 cm$^{-1}$.

NMR (CDCl$_3$): 1.25–1.39 (10H, m, CH$_2$×5), 2.55–2.58 (2H, m, C$\underline{H}_2$NH$_2$), 2.90–2.95 (2H, m, C$\underline{H}_2$NHCONH$_2$), 5.35 (2H, s, NHCON$\underline{H}_2$), and 5.93 (1H, br, CH$_2$$\underline{NH}$CONH$_2$).

Step 4

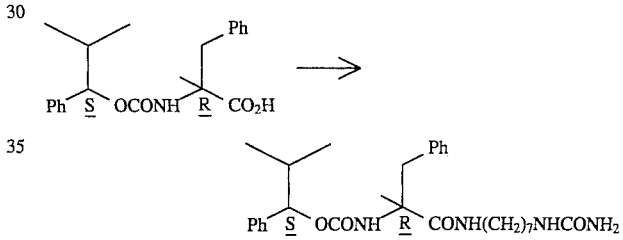

The acid (prepared Example 12, Step 1) (50 mg, 0.14 mmol), HBTU (53 mg, 0.14 mmol) and DIPEA (68 µL, 0.28 mmol) were dissolved in DMF (3 mL), and the solution was stirred for 20 minutes. The amine (25 mg, 0.14 mmol) was added, and stirring was continued for 4 hours. The solvent was removed in vacuo, and the residue was taken up in EtOAc (40 mL). The solution was washed with 2M HCl (2×30 mL), 10% Na$_2$CO$_3$ aqueous (2×30 mL), brine (30 mL), and dried over MgSO$_4$. The solvent was removed in vacuo, and the residue was purified by column chromatography 80% EtOAc:heptane followed by 10% MeOH:EtOAc. A white solid was obtained 30 mg (43%), mp 54°–57° C.

IR: 3347, 2931, 1713, 1651, and 1538 cm$^{-1}$.

NMR (CDCl$_3$): 0.79 (3H, d, J=6.8 Hz, C$\underline{H}_3$CHCH$_3$), 0.98 (3H, d, J=6.8 Hz, CH$_3$CHC$\underline{H}_3$), 1.21–1.60 (13H, m, αCH$_3$, CH$_2$×5), 2.07 (1H, m, CH$_3$C$\underline{H}$CH$_3$), 3.05 (1H, d, J=13.6 Hz, PhC$\underline{H}$H), 3.32 (1H, d, J=13.6 Hz, PhCH$\underline{H}$), 3.14–3.22 (4H, m, CONHC$\underline{H}_2$, C$\underline{H}_2$NHCONH$_2$), 4.42 (2H, br s, CONH$_2$), 4.85 (1H, br s, $\underline{NH}$CONH$_2$), 5.09 (1H, s, urethane NH), 5.37 (1H, d, J=7.6 Hz, PhC$\underline{H}$), 6.28 (1H, br s, amide NH), and 6.92–7.38 (10H, m, aromatics).

Analysis calculated for C$_{29}$H$_{42}$N$_4$O$_4$·0.6 H$_2$O: C, 66.79; H, 8.35; N, 10.74. Found: C, 66.69; H, 8.09; N, 10.68.

EXAMPLE 8

[2-(2-Fluoro-phenyl)-1-methyl-1-(7-ureido-heptylcarbamoyl)-ethyl]-carbamic acid 2-methyl-1-phenyl-propyl ester

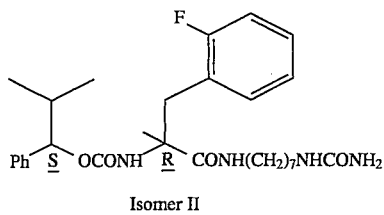

Isomer II

Step 1

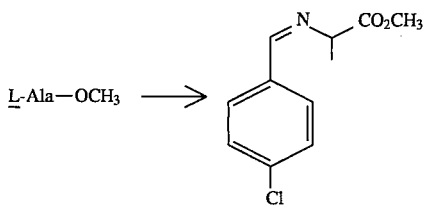

To a suspension of L-alanine methyl ester (5 g, 36 mmol), MgSO₄ (2 g), and 4-chlorobenzaldehyde (51 g, 36 mmol) in DCM (60 mL) was added triethylamine (5 mL), 36 mmol). The reaction mixture was stirred for 20 hours, filtered, and concentrated in vacuo. The resulting gum was triturated with ether, and the precipitate was then removed by filtration. The filtrate was concentrated to yield the desired product as a colorless oil 7.90 g (98%).

IR (film): 2952 and 1743 cm⁻¹.

NMR (CDCl₃): 1.52 (3H, d, J=6.8 Hz, CH₃), 3.75 (3H, s, OCH₃), 4.16 (1H, q, αCH), 7.39 (2H, d, J=8.8 Hz, H-aromatic), 7.72 (2H, d, J=8.8 Hz, H-aromatic), and 8.27 (1H, s, CH=N).

Step 2

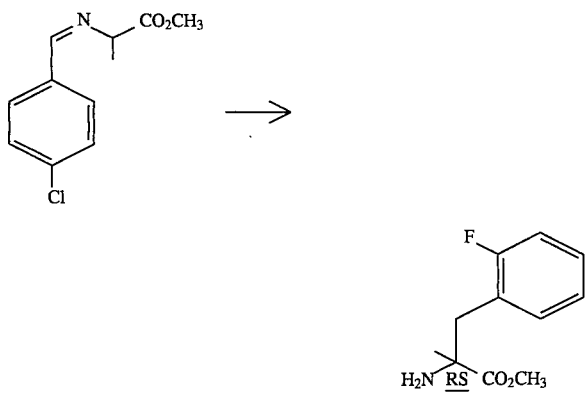

To a solution of the Schiff base (2 g, 8.9 mmol) in THF (20 mL) at −70° C., under N₂ was added LHMDS (9.75 mL of 1M in THF, 9.7 mmol). The reaction mixture was stirred for 1.25 hours at −70° C. and 2-fluorobenzylbromide (1.67 g, 8.9 mmol) was then added dropwise in THF (5 mL). The reaction was allowed to warm to room temperature, and stirring was continued for 15 hours. 1M HCl (10 mL) was added, and stirring was continued for a further 24 hours. The solvent was removed in vacuo, and the residue was partitioned between EtOAc (200 mL) and 1M HCl (200 mL). The aqueous layer was made basic with Na₂CO₃ and was extracted with EtOAc (3×100 mL). The combined extracts were dried over MgSO₄, and the solvent was removed in vacuo to give an oil 1.54 g (82%).

IR (film): 2952 and 1735 cm⁻¹.

NMR (CDCl₃): 1.39 (3H, s, αCH₃), 2.93 (1H, d, J=13.6 Hz, βCHH), 3.09 (1H, d, J=13.6 Hz, βCHH), 3.72 (3H, s, OCH₃), and 7.00–7.25 (4H, m, aromatics).

Step 3

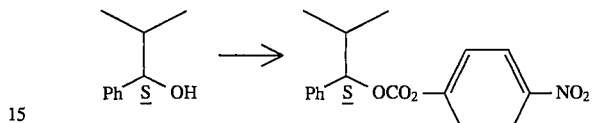

The 4-nitrophenol carbonate was prepared as described for Intermediate XIV, Step 1, 0.56 g (53%).

IR (film): 3119 and 1766 cm⁻¹.

NMR (CDCl₃): 0.85 (3H, d, J=6.8 Hz, CH₃CHCH₃), 1.09 (3H, d, J=6.8 Hz, CH₃CHCH₃), 2.24 (1H, m, CH₃CHCH₃), 5.37 (1H, d, J=8 Hz, PhCH), 7.31–7.41 (7H, m, aromatics), and 8.23 (2H, d, J=9.2 Hz, aromatics).

Step 4

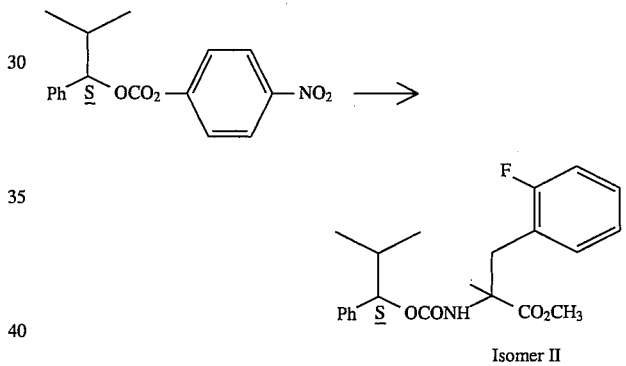

Isomer II

The carbonate (0.52 g, 1.7 mmol) was dissolved in DMF (4 mL), and the RS-alphamethyl-2F-phenylalanine methyl ester (0.42 g, 2 mmol) was added. The solution was stirred for 10 days, and the solvent was then removed in vacuo. The residue was dissolved in EtOAc (100 mL), and the solution was washed with 10% K₂CO₃ (5×75 mL) and brine (75 mL). The organic was dried over MgSO₄, and the solvent was concentrated in vacuo. The residue was purified, and the diastereoisomers were separated by column chromatography, 10% ether:heptane.

Isomer I: 196 mg, 30%.

Isomer II: 165 mg, 26%.

Isomer III:

IR (film): 3354, 2960, 1739, and 1717 cm⁻¹.

NMR (CDCl₃): 0.81 (3H, d, J=6.8 Hz, CH₃CHCH₃), 0.97 (3H, d, J=6.8 Hz, CH₃CHCH₃), 1.54 (3H, s, αCH₃), 2.08 (1H, m, CH₃CHCH₃), 3.25 (1H, d, J=13.6 Hz, PhCHH), 3.40 (1H, d, J=13.6 Hz, PhCHH), 3.73 (3H, s, OCH₃), 5.39 (2H, m, PhCH, urethane NH), and 6.86–7.36 (9H, m, aromatics).

Step 5

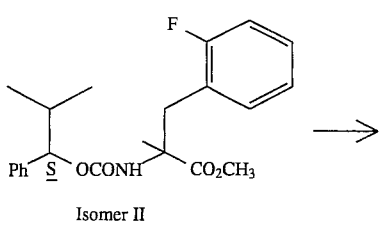

Isomer II

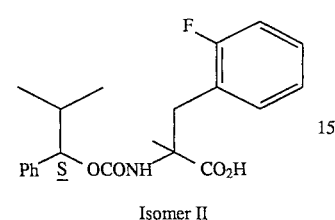

Isomer II

The ester (0.13 g, 0.35 mmol) was dissolved in THF (4 mL) and 1M LiOH (1 mL) was added. The reaction mixture was stirred for 4 days, and the solvent was then removed in vacuo. The residue was dissolved in H$_2$O (100 mL), and the pH of the solution was adjusted to 3 with 1M HCl. The solution was extracted with EtOAc (3×75 mL), and the combined extracts were washed with water (100 mL). The organic phase was dried over MgSO$_4$, and the solvent was removed in vacuo to give a white foam 127 mg (97%).

IR (film): 2964, 1714, and 1494 cm$^{-1}$.

NMR (CDCl$_3$): 0.81 (3H, d, J=6.8 Hz, C$\underline{H}_3$CHCH$_3$), 0.98 (3H, d, J=6.8 Hz, CH$_3$CHC$\underline{H}_3$), 1.52 (3H, s, αCH$_3$), 2.07 (1H, m, CH$_3$C$\underline{H}$CH$_3$), 3.34 (2H, m, βCH$_2$), 5.22 (1H, s, urethane NH), 5.39 (1H, d, J=7.2 Hz, PhC$\underline{H}$), and 6.85–7.38 (9H, m, aromatics).

Step 6

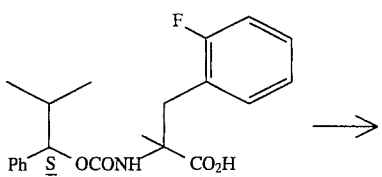

Isomer II

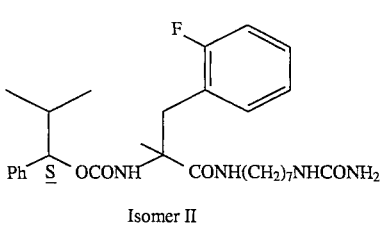

Isomer II

The acid (40 mg, 0.11 mmol), HBTU (42 mg, 0.11 mmol), and DIPEA (19 μL, 0.11 mmol) were dissolved in DMF (1 mL). The solution was stirred for 10 minutes, then the amino urea (prepared Example 7, Step 3) (23 mg, 0.13 mmol) and DIPEA (19 μL, 0.11 mmol) were added. The reaction mixture was stirred for 15 hours, and the solvent was then removed in vacuo. The residue was dissolved in EtOAc (100 mL), and the organic was washed with 1M HCl (3×75 mL), saturated NaHCO$_3$ (3×75 mL), H$_2$O (75 mL), and brine (75 mL). The organic was dried over MgSO$_4$, and the solvent was removed in vacuo. The residue was purified by column chromatography 5% MeOH in DCM to give a white foam 17 mg (29%), mp 67°–72° C.

IR (film): 3343, 2932, 2858, 1713, 1651, and 1539 cm$^{-1}$.

NMR (CDCl$_3$): 0.81 (3H, d, J=6.4 Hz, C$\underline{H}_3$CHCH$_3$), 1.00 (3H, d, J=6.8 Hz, CH$_3$CHC$\underline{H}_3$), 1.20–1.58 (13H, m, αCH$_3$, CH$_2$×5), 2.10 (1H, m, CH$_3$C$\underline{H}$CH$_3$), 3.10–3.30 (6H, m, βCH$_2$, CONHC$\underline{H}_2$, C$\underline{H}_2$NHCONH$_2$), 4.48 (2H, br s, CON$\underline{H}_2$), 4.98 (1H, br, OCON$\underline{H}$), 5.38 (2H, m, PhC$\underline{H}$, N$\underline{H}$CONH$_2$), 6.22 (1H, br, amide N$\underline{H}$), and 6.82–7.36 (9H, m, aromatics).

HPLC: 40–100% B over 20 minutes, A=H$_2$O, B=CH$_3$CN; 0.1% TFA R$_t$=13.21 minutes.

Analysis calculated for C$_{29}$H$_{41}$N$_4$O$_4$F.0.3 H$_2$O: C, 65.22; H, 7.85; N, 10.49. Found: C, 65.23; H, 7.77; N, 10.36.

EXAMPLE 9

[2-(2,3-Difluoro-phenyl)-1-methyl-1-(7-ureido-heptylcarbamoyl)-ethyl]-carbamic acid 2-methyl-1-phenyl-propyl ester

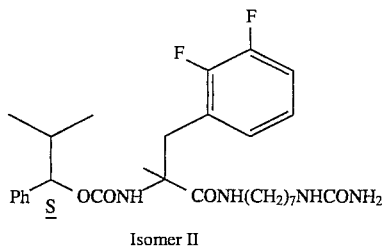

Isomer II

Step 1

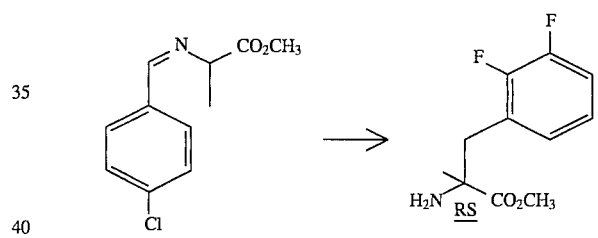

The compound was prepared following the procedure described for Example 8, Step 2, using the Schiff base prepared in Example 8, Step 1 (0.5 g, 2.2 mmol). The product was obtained as an oil 382 mg (75%).

IR (film): 3378, 2954, 1735, 1491, and 1206 cm$^{-1}$.

NMR (CDCl$_3$): 1.40 (3H, s, αCH$_3$), 2.96 (1H, d, J=13 Hz, αC$\underline{H}$H), 3.12 (1H, d, J=13 Hz, βCH$\underline{H}$), 3.72 (3H, s, OCH$_3$), and 6.92–7.08 (3H, m, aromatics).

Step 2

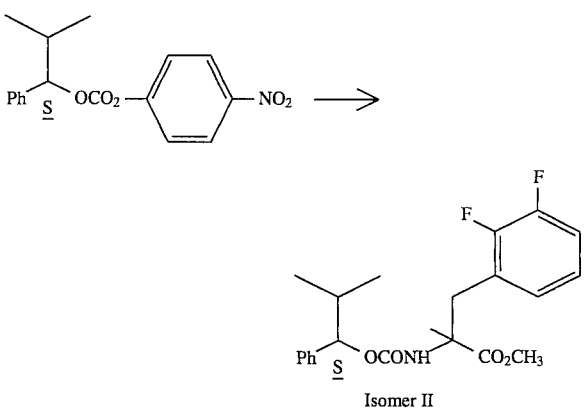

Isomer II

The desired product was prepared by the procedure described for Example 8, Step 4, using the carbonate prepared in Example 8, Step 3 (250 mg, 0.79 mmol). An analogous resolution was carried out to give the desired Isomer II as a white solid 111 mg (35%), mp 112°–115° C.

IR: 3343, 2957, 1735, 1713, 1492, 1268, and 1071 cm$^{-1}$.

NMR (CDCl$_3$): 0.81 (3H, d, J=6.8 Hz, C$\underline{H}_3$CHCH$_3$), 0.98 (3H, d, J=6.8 Hz, CH$_3$CHC$\underline{H}_3$), 1.54 (3H, s, αCH$_3$), 2.07 (1H, m, CH$_3$C$\underline{H}$CH$_3$), 3.29 (1H, d, J=14 Hz, PhC$\underline{H}$H), 3.46 (1H, d, J=14 Hz, PhCH$\underline{H}$), 3.76 (3H, s, OCH$_3$), 5.38 (2H, m, PhC$\underline{H}$, urethane NH), 6.65 (1H, m, aromatic), 6.85 (1H, m, aromatic), 7.02 (1H, m, aromatic), and 7.26–7.36 (5H, m, Ph aromatics).

M/S (CI): 406, 230, and 133.

Analysis calculated for C$_{22}$H$_{25}$NO$_4$F$_2$: C, 65.17; H, 6.21; N, 3.45. Found: C, 65.22; H, 6.26; N, 3.43.

Step 3

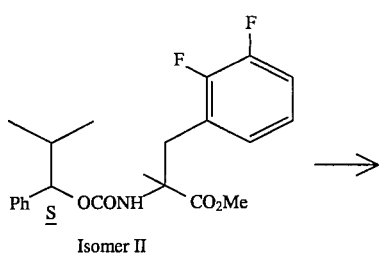

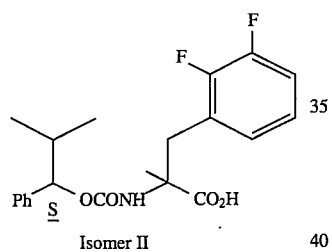

The desired compound was prepared following the procedure described for Example 8, Step 5. The product was obtained as a white foam 94 mg (92%).

IR (film): 3418, 3035, 2965, 1715, and 1493 cm$^{-1}$.

NMR (CDCl$_3$): 0.80 (3H, d, J=6.8 Hz, C$\underline{H}_3$CHCH$_3$), 0.98 (3H, d, J=6.8 Hz, CH$_3$CHC$\underline{H}_3$), 1.52 (1H, s, αCH$_3$), 2.08 (1H, m, Ch$_3$C$\underline{H}$CH$_3$), 3.35 (1H, d, J=13.6 Hz, ArC$\underline{H}$H), 3.42 (1H, d, J=13.6 Hz, ArCH$\underline{H}$), 5.21 (1H, br, urethane NH), 5.38 (1H, br d, PhC$\underline{H}$), 6.57 (1H, br, aromatic), 6.82 (1H, br, aromatic), 7.02 (1H, br, aromatic), and 7.26–7.38 (5H, m, aromatics).

Step 4

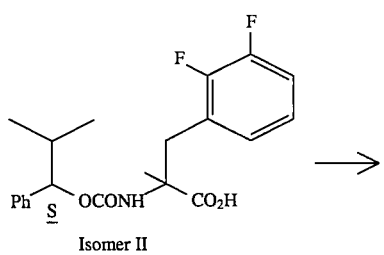

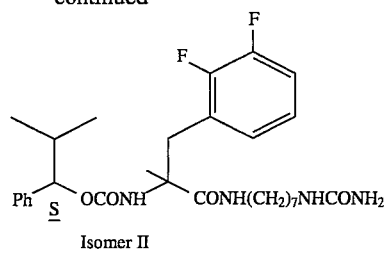

The acid (50 mg, 0.13 mmol) was coupled to the amino urea (prepared Example 7, Step 3) (28 mg, 0.16 mmol) following the procedure described for Example 8, Step 6, yield 39 mg (55%), mp 59°–64° C.

IR (film): 3363, 2932, 2864, 1709, 1651, and 1539 cm$^{-1}$.

m/e (APCI): 1050, 547, and 504.

NMR (CDCl$_3$): 0.80 (3H, d, J=6.8 Hz, C$\underline{H}_3$CHCH$_3$), 0.99 (3H, d, J=6.8 Hz, CH$_3$CHC$\underline{H}_3$), 1.26–1.57 (13H, m, αCH$_3$, CH$_2$×5), 2.09 (1H, m, CH$_3$C$\underline{H}$CH$_3$), 3.19 (4H, m, CONH C$\underline{H}_2$, C$\underline{H}_2$NHCONH$_2$), 3.26 (1H, d, J=14 Hz, PhC$\underline{H}$H), 3.36 (1H, d, J=14 Hz, PhCH$\underline{H}$), 4.40 (2H, br, NHCON$\underline{H}_2$), 4.80 (1H, br, N$\underline{H}$CONH$_2$), 5.28 (1H, br, urethane NH), 5.37 (1H, br d, PhC$\underline{H}$), 6.25 (1H, br, amide NH), 6.55 (1H, br, aromatic), 6.76 (1H, br, aromatic), 7.00 (1H, m, aromatic), and 7.26–7.38 (5H, m, Ph).

Analysis calculated for C$_{29}$H$_{40}$N$_4$O$_4$F$_2$·0.75 H$_2$O: C, 62.18; H, 7.47; N, 10.00. Found: C, 61.17; H, 7.20; N, 9.80.

EXAMPLE 10

[2-Benzofuran-3-yl-1-methyl-1-(7-ureido-heptylcarbamoyl)-ethyl]-carbamic acid 2-methyl-1-phenyl-propyl ester

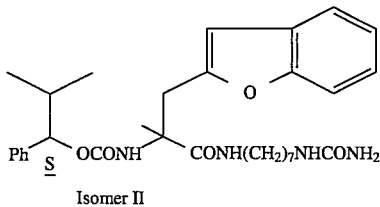

Step 1

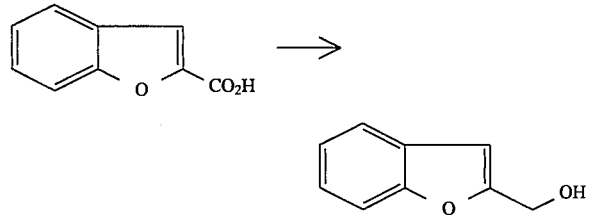

A solution of 4-methylmorpholine (1.5 mL, 13.6 mmol) in anhydrous THF (25 mL) was added dropwise over 1 hour to a stirred solution of benzo[b]furan-2-carboxylic acid (2.0 g, 12.3 mmol) and ethylchloroformate (1.30 mL, 13.6 mmol) in THF (50 mL) cooled in a salt ice bath. The mixture was stirred for 1 hour, and then the precipitate was removed by filtration. The filtrate was re-cooled, and a solution of 2M LiBH$_4$ in THF (18.5 mL, 37 mmol) was added dropwise over 20 minutes. The reaction mixture was stirred for 2 hours, and then 1N HCl (25 mL) was slowly added. The THF was removed in vacuo, and the aqueous then extracted with EtOAc (2×50 mL). The combined extracts were washed with brine (25 mL) and then dried over MgSO₄. The residue was purified by column chromatography 75% n-hexane, 25% EtOAc, yield 1.53 g (84%).

IR (film): 3346, 2922, 2862, 1606, 1454, 1255, 1012, and 752 cm$^{-1}$.

NMR (CDCl₃): 1.98 (1H, t, J=6.0 Hz, CH₂OH), 4.77 (2H, d, J=6.0 Hz, CH₂OH), 6.66 (1H, s, H₃-aromatic), 7.20–7.30 (2H, m, H₅, H₆-aromatic), 7.46 (1H, d, J=8 Hz, H₇-aromatic), and 7.55 (1H, d, J=7.6 Hz, H₄-aromatic).

Step 2

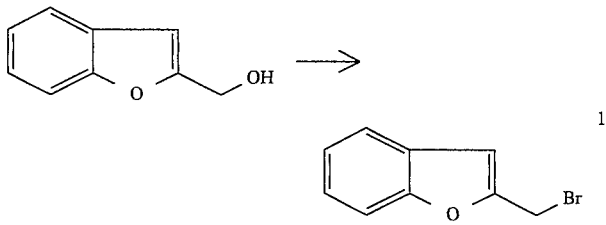

A solution of bromine (0.42 mL, 8.2 mmol) in DMF (5 mL) was added dropwise over 5 minutes to a cooled stirred solution of the alcohol (1.16 g, 7.8 mmol) and triphenylphosphine (2.15 g, 8.2 mmol) in anhydrous DMF (10 mL) under an atmosphere of N₂. The reaction mixture was stirred overnight and then diluted with water (150 mL). The solution was extracted with EtOAc (3×100 mL) and the combined extracts were then washed once with brine (50 mL) and dried over MgSO₄. The solvent was reduced in vacuo and the residue then precipitated with heptane. The solid was removed by filtration, and the filtrate was concentrated in vacuo. The product was purified by column chromatography 10% DCM in heptane to give the desired bromide 587 mg (36%).

IR (film): 1584, 1452, 1475, 1422, 1282, 1254, 1208, 1189, and 953 cm$^{-1}$.

NMR (CDCl₃): 4.60 (2H, s, CH₂Br), 6.75 (1H, s, aromatic), 7.21–7.34 (2H, m, aromatics), and 7.47–7.56 (2H, m, aromatics).

Step 3

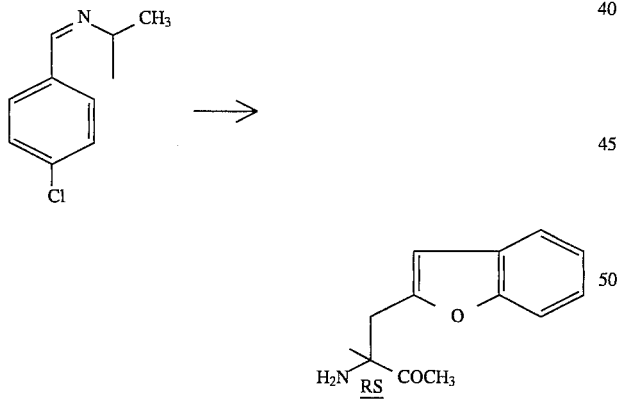

The amino acid was prepared following the procedure described for Example 8, Step 2, using the Schiff base (prepared in Example 8, Step 1) (547 mg, 2.4 mmol) and the bromide (511 mg, 2.4 mmol). The desired product was obtained as an oil 326 mg (58%).

IR (film): 3376, 2951, 1733, 1586, 1455, 1253, 1212, 1106, 816, and 751 cm$^{-1}$.

NMR (CDCl₃): 1.45 (3H, s, CH₃), 1.70 (2H, b, NH₂), 3.02 (1H, d, J=14.4 Hz, ArCHH), 3.29 (1H, d, J=14.4 Hz, ArCHH), 3.75 (3H, s, OCH₃), 6.49 (1H, s, aromatic), 7.16–7.25 (2H, m, aromatics), 7.39–7.41 (1H, m, aromatic), and 7.48–7.51 (1H, m, aromatic).

Analysis calculated for C₁₃H₁₅NO₃.0.25 H₂O: C, 65.67; H, 6.57; N, 5.89. Found: C, 65.71; H, 6.45; N, 5.80.

Step 4

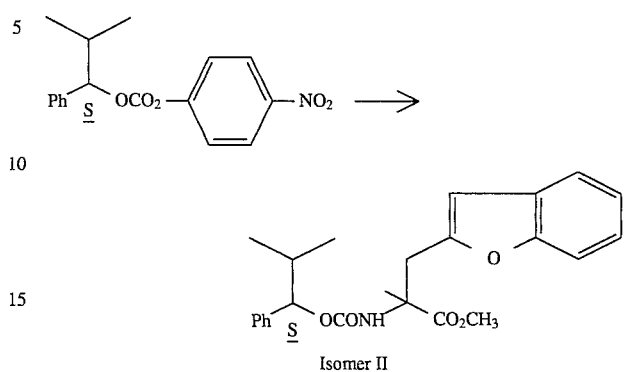

The desired product was prepared by the procedure described for Example 8, Step 4 using the carbonate prepared in Example 8, Step 3 (250 mg, 0.8 mmol). The mixture obtained was resolved by column chromatography 10% ether in heptane followed by 20% ether in heptane. Isomer II was obtained as a white solid 80 mg (25%), mp 101°–107° C.

IR (film): 3420, 3356, 2958, 2932, 2873, 1740, 1721, 1497, 1455, 1253, 1122, 1056, and 751 cm$^{-1}$.

NMR (CDCl₃): 0.80 (3H, d, J=6.8 Hz, CH₃CHCH₃), 0.95 (3H, d, J=6.8 Hz, CH₃CHCH₃), 1.60 (3H, s, αCH₃), 2.07 (1H, m, CH₃CHCH₃), 3.43 (1H, d, J=14.8 Hz, ArCHH), 3.61 (1H, d, J=14.0 Hz, ArCHH), 3.80 (3H, s, OCH₃), 5.40 (1H, d, J=6.8 Hz, PhCH), 5.53 (1H, br, urethane NH), 6.27 (1H, s, aromatic), 7.16–7.36 (8H, m, aromatic), and 7.43–7.46 (1H, m, aromatic).

Step 5

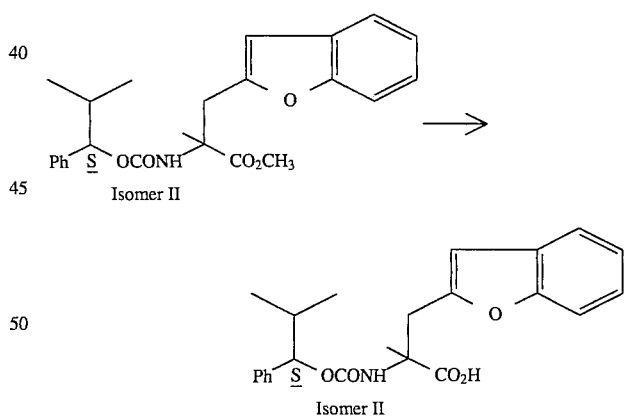

The desired compound was prepared following the procedure described for Example 8, Step 5. The product was obtained as a solid 43 mg (60%), mp 69°–73° C.

IR (film): 3409, 2962, 1716, 1507, 1455, 1253, 1057, and 752 cm$^{-1}$.

NMR (DMSO-d₆): 0.78 (3H, d, J=6.4 Hz, CH₃CHCH₃), 0.89 (3H, d, J=6.4 Hz, CH₃CHCH₃), 1.34 (3H, s, αCH₃), 1.99–2.05 (1H, m, CH₃CHCH₃), 3.08 (1H, d, J=14.8 Hz, ArCHH), 3.49 (1H, d, J=14.8 Hz, ArCHH), 5.33 (1H, d, J=6.4 Hz, PhCH), 6.16 (1H, s, aromatic), and 7.18–7.50 (10H, m, aromatics, NHCO). $[\alpha]_D^{20}$=+68.4 (C=0.25, acetone).

Step 6

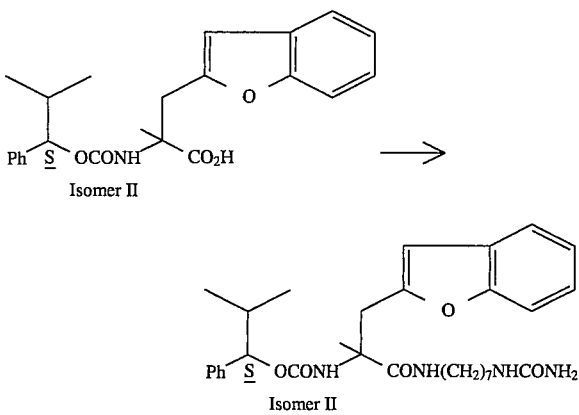

The acid (35 mg, 0.09 mmol) was coupled to the amino urea (prepared Example 7, Step 3) (16 mg, 0.09 mmol) following the procedure described for Example 8, Step 6, yield 25 mg (51%).

IR (film): 3494, 3350, 2931, 2857, 1709, 1651, 1602, 1543, 1455, 1383, 1335, 1254, 1054, 910, and 735 cm$^{-1}$.

$[\alpha]_D^{20}$=+68.7° (C=0.31, acetone).

NMR (CDCl$_3$): 0.80 (3H, d, J=6.8 Hz, C$\underline{H}_3$CHCH$_3$), 0.97 (3H, d, J=6.6 Hz, CH$_3$CHC$\underline{H}_3$), 1.26–1.51 (10H, m, 5×CH$_2$), 1.51 (3H, s, αCH$_3$), 2.02–2.17 (1H, m, CH$_3$C$\underline{H}$CH$_3$), 3.08–3.19 (4H, m, CONHC$\underline{H}_2$, C$\underline{H}_2$NHCONH$_2$), 3.30 (1H, d, J=14.8 Hz, ArC$\underline{H}$H), 3.54 (1H, d, J=14.8 Hz, ArCH$\underline{H}$), 4.60 (2H, s, NHCON$\underline{H}_2$), 5.17 (1H, b, urethane NH), 5.39 (1H, d, J=7.6 Hz, PhC$\underline{H}$), 5.48 (1H, s, aromatic), 6.19 (1H, br, N$\underline{H}$CONH$_2$), 6.47 (1H, b, amide NH), and 7.15–7.42 (9H, m, aromatics).

Analysis calculated for C$_{31}$H$_{42}$N$_4$O$_5$·0.25 H$_2$O: C, 67.06; H, 7.72; N, 10.09. Found: C, 67.12; H, 7.64; N, 9.95.

EXAMPLE 11

{2-(2,3-Difluoro-phenyl)-1-methyl-1-[3-{3-ureido-propoxy)-propylcarbamoyl]-ethyl}-carbamic acid 2-methyl-1-phenyl-propyl ester

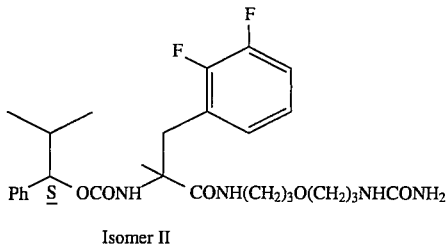

Step 1

Bis-(3-aminopropyl)ether (4.89 g, 37 mmol) was dissolved in 1.4-dioxane (1.5 L) and Na$_2$CO$_3$ (3.16 g, 11 mmol) in H$_2$O (150 mL) was added. The solution was cooled on a salt ice bath and benzylchloroformate (1.5 mL, 7.4 mmol) in 1,4-dioxane (100 mL) was added over 2.5 hours. The reaction mixture was stirred for 15 hours, after which the solvent was removed in vacuo. The residue was dissolved in EtOAc (100 mL), and the solution was washed with brine (3×75 mL), then dried over MgSO$_4$. Removal of the solvent gave a white solid 2.01 g.

IR (film): 3333, 2943, 2868, 1704, 1538, and 1260 cm$^{-1}$.
Step 2

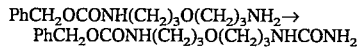

The amine (2.03 g, 7.4 mmol) was dissolved in THF (20 mL) and trimethylsilylisocyanate (935 μL, 7.4 mmol) was added dropwise over 15 minutes under an atmosphere of nitrogen. The reaction mixture was stirred for 3.5 hours, after which a further aliquot of trimethylsilylisocyanate (500 μL, 3.7 mmol) was added. Stirring was continued for a further 15 hours, and the solvent was then removed in vacuo. The residue was dissolved in EtOAc (50 mL) and washed with brine (2×25 mL), then dried over MgSO$_4$. The solvent was removed in vacuo, and the residue was recrystallized from EtOAc to give a white solid 0.31 g (13%).

IR (film): 3339, 2943, 2869, 1703, 1657, 1607, 1548, 1261, and 1113 cm$^{-1}$.

NMR (CDCl$_3$): 1.75 (4H, m, CH$_2$C$\underline{H}_2$CH$_2$×2), 3.34 (4H, m, CONHC$\underline{H}_2$, C$\underline{H}_2$NHCO), 3.49 (4H, m, C$\underline{H}_2$O×2), 4.59 (2H, br s, CON$\underline{H}_2$), 5.08 (3H, m, PhC$\underline{H}_2$, CH$_2$N$\underline{H}$CO), 5.65 (1H, br, urethane NH), and 7.26–7.52 (5H, m, aromatics).
Step 3

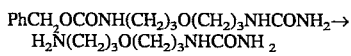

The urea (294 mg, 0.95 mmol) was dissolved in ethanol (60 mL) and Pearlman's catalyst (30 mg) was added. The reaction mixture was hydrogenated at 47 psi, H$_2$, at 30° C. for 3 hours, and the catalyst was then removed by filtration through kieselguhr. The solvent was removed in vacuo to give a sticky solid 152 mg (92%).

IR (film): 3350, 2940, 2871, 1652, 1574, 1346, and 1109 cm$^{-1}$.

NMR (CDCl$_3$): 1.73 (4H, m, CH$_2$C$\underline{H}_2$CH$_2$×2), 2.80 (2H, t, J=6.8 Hz, C$\underline{H}_2$NH$_2$), 3.18 (2H, t, J=6.8 Hz, C$\underline{H}_2$NHCONH$_2$), and 3.51 (4H, m, C$\underline{H}_2$O×2).
Step 4

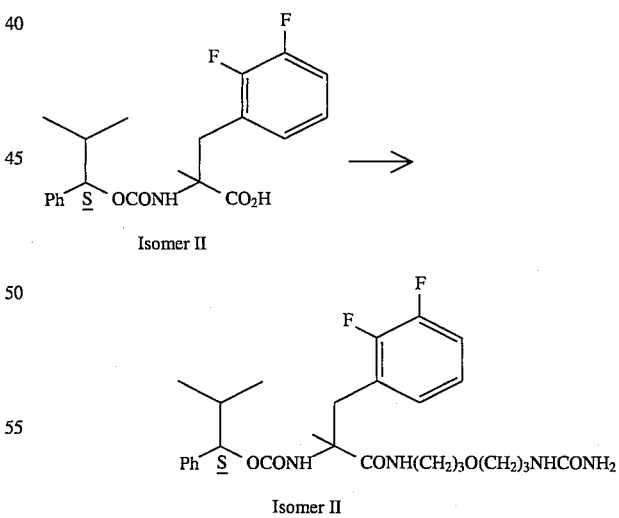

The acid (prepared Example 9, Step 3) (40 mg, 0.1 mmol), HBTU (39 mg, 0.1 mmol), and DIPEA (18 μL, 0.1 mmol) were dissolved in DMF (2 mL). The solution was stirred for 2 minutes, and then the amino urea (19 mg, 0.11 mmol) and DIPEA (18 μL, 0.1 mmol) were added. The reaction mixture was stirred for 8 hours, and the solvent was then removed in vacuo. The residue was dissolved in EtOAc (50 mL), and the solution was washed with 1M HCl (2×30 mL), saturated NaHCO₃ (2×30 mL), and brine (30 mL). The organic was dried over MgSO₄, and the solvent was removed in vacuo. The product was purified by column chromatography 5% MeOH in DCM to give a white solid 38 mg (69%), mp 58°–62° C.

IR (film): 3341, 2937, 2872, 1714, 1652, 1607, and 1539 cm⁻¹.

NMR (CDCl₃): 0.80 (3H, d, J=6.6 Hz, C<u>H</u>₃CHCH₃), 0.99 (3H, d, J=6.8 Hz, CH₃CHC<u>H</u>₃), 1.43 (3H, 3, αCH₃), 1.58–1.74 (4H, m, CH₂C<u>H</u>₂CH₂×2), 2.08 (1H, m, CH₃C<u>H</u>CH₃), 3.29–3.45 (10H, m, ARC<u>H</u>₂, C<u>H</u>₂NHCONH₂, C<u>H</u>₂O×2, CONHC<u>H</u>₂), 4.65 (2H, s, CON<u>H</u>₂), 5.31 (1H, s, urethane NH), 5.37 (1H, d, J=7.3 Hz, PhC<u>H</u>), 5.73 (1H, br, N<u>H</u>CONH₂), 6.54 (1H, br, amide NH), 6.63 (1H, br, aromatic), 6.78 (1H, br, aromatic), 7.01 (1H, m, aromatic), and 7.26–7.38 (5H, m, Ph).

Analysis calculated for C₂₈H₃₈N₄O₅F₂: C, 61.30; H, 6.98; N, 10.21. Found: C, 61.05; H, 7.11; N, 10.06.

SYNTHESIS OF INTERMEDIATES XIV AND XV

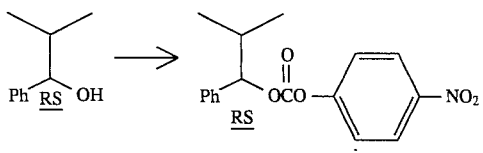

Step 1

4-Nitrophenylchloroformate (8.05 g, 39.9 mmol) in dichloromethane (40 mL) was added dropwise to a solution of (RS)-2-methyl-1-phenyl-1-propanol (6.00 g, 39.9 mmol) and pyridine (3.23 mL, 39.9 mmol) in dichloromethane (100 mL) at 0° C. The solution was allowed to warm to room temperature and stirred for 2 days. The reaction mixture was washed with water and 2M HCl and dried (MgSO₄). Further purification by column chromatography using 20% diethyl ether:hexane gave the carbonate as an off-white solid (7.50 g, 60%).

IR (film): 2967, 1762, 1525, 1346, and 1216 cm⁻¹.

H¹NMR (CDCl₃): δ0.85 (3H, d, J=7 Hz, —CH₃), 1.09 (3H, d, J=6 Hz, —CH₃), 2.24 (1H, m, (CH₃)₂C<u>H</u>), 5.37 (1H, d, J=7 Hz, PhC<u>H</u>), 7.36 (7H, m, Ar), and 8.24 (2H, m, Ar).

Step 2

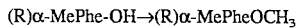

Methanol (120 mL) was cooled to –5° C. and thionyl chloride (14 mL, 195 mmol) was added slowly over 5 minutes followed by the addition of (R)-α-MePhe-OH (7.00 g, 39 mmol). The resulting suspension was allowed to warm to room temperature, stirred for 16 hours, and heated at reflux for 1.5 hours. On cooling, the mixture was evaporated to a white solid which was taken up in ethyl acetate (200 mL) and washed with saturated NaHCO₃ (2×100 mL). Drying (MgSO₄) and evaporation gave a pale yellow liquid (4.8 g, 64%).

IR (film): 3030, 2951, 1733, 1603, and 1453 cm⁻¹.

¹H NMR (CDCl₃): δ1.60 (3H, s, αMe), 2.80 (1H, d, J=13.2 Hz, PhCH<u>H</u>), 3.13 (1H, d, J=13.2 Hz), 3.70 (3H, s, OCH₃), and 7.12–7.31 (5H, m, Ar).

Step 3

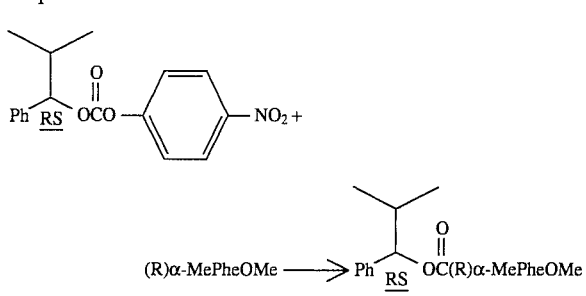

The carbonate (3.00 g, 9.5 mmol), (R)-αMePheOMe (1.84 g, 9.5 mmol) and triethylamine (1.33 mL, 9.5 mmol) were dissolved in DMF (20 mL) and stirred at room temperature for 3 days. On removal of the solvent, the residue was taken up in ethyl acetate (100 mL) and washed with 2M HCl (2×70 mL) and brine (70 mL). Drying (MgSO₄) and evaporation gave a colorless oil which was purified by column chromatography on silica using 6% diethyl ether:hexane giving i) a colorless oil (1.0 g) (R, R isomer); Intermediate XV
IR (film): 3423, 2960, 1740, 1721, 1496, and 1451 cm⁻¹.
¹H NMR (CDCl₃): δ0.81 (3H, d, J=6.8 Hz, —CH₃), 0.98 (3H, d, J=6.4 Hz, —CH₃), 1.66 (3H, s, αCH₃), 2.03–2.10 (1H, m, (CH₃)₂C<u>H</u>), 3.05 (1H, d, J=13.6 Hz, PhCH<u>H</u>), 3.40 (1H, d, J=13.2 Hz, PhC<u>H</u>H), 3.72 (3H, s, CO₂CH₃), 5.35 (1H, d, J=6.8 Hz, PhC<u>H</u>OCO), 5.55 (1H, bs, urethane), 6.76–6.77 (2H, m, Ph), and 7.08–7.40 (8H, m, Ph).
M⁺: 133, 194, 238, and 370.
[α]<sub>D</sub>²⁰=+21.4° (C=0.25, acetone).

ii) a white solid (0.68 g (<u>S</u>, R isomer); Intermediate XIV, mp=118.5°–120° C.
IR (film): 3353, 2959, 1732, 1714, 1497, and 1451 cm⁻¹.
¹H NMR (CDCl₃): δ0.83 (3H, d, J=6.8 Hz, —CH₃), 0.99 (3H, d, J=6.6 Hz, —CH₃), 1.55 (3H, s, αCH₃), 2.06–2.11 (1H, m, (CH₃)₂C<u>H</u>), 3.19 (1H, d, J=13.4 Hz, PhCH<u>H</u>), 3.39 (1H, d, J=13.4 Hz, PhC<u>H</u>H), 3.75 (3H, s, CO₂CH₃), 5.41 (2H, m, urethane, PhC<u>H</u>OCO), 6.96–6.98 (2H, m, Ph), and 7.18–7.37 (8H, m, Ph).
M⁺: 91, 133, 194, 238, and 370.
[α]<sub>D</sub>²⁰=+45.6° (C=0.475, acetone).

SYNTHESIS OF EXAMPLE 12

{1-[1-(6-Hydroxy-hexylcarbamoyl)-2-(4-hydroxy-phenyl)-ethylcarbamoyl]-1-methyl-2-phenyl-ethyl}-carbamic acid 2-methyl-1-phenyl-propyl ester

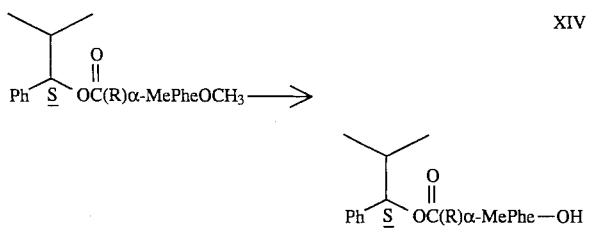

Step 1

The methyl ester (0.74 g, 2 mmol) (Intermediate XIV) was dissolved in THF (20 mL). Lithium hydroxide monohydrate (0.16 g, 4 mmol) in water (4 mL) was added, and the mixture was heated at reflux for 48 hours. On removal of the solvents, the residue was partitioned between 2M HCl and ethyl acetate. The aqueous layer was re-extracted with ethyl acetate, and the combined organics were dried (MgSO₄) and evaporated down to a colorless oil (0.61 g, 86%).

IR (film): 3409, 2969, 1713, 1497, 1452, and 1052 cm⁻¹.

¹H NMR (CDCl₃): δ0.82 (3H, d, J=6.8 Hz, —CH₃), 0.99 (3H, d, J=6.4 Hz, —CH₃), 1.55 (3H, s, αCH₃), 2.10 (1H, m, (CH₃)₂C$\underline{H}$), 3.29 (2H, m, PhC$\underline{H}_2$), 5.27 (1H, bs, urethane), 5.42 (1H, d, J=7.2 Hz, PhC$\underline{H}$OCO), 6.99 (2H, m, Ar), and 7.17–7.38 (8H, m, Ar).

m/e (CI): 356, 302, 266, 180, 133, and 91.

Step 2

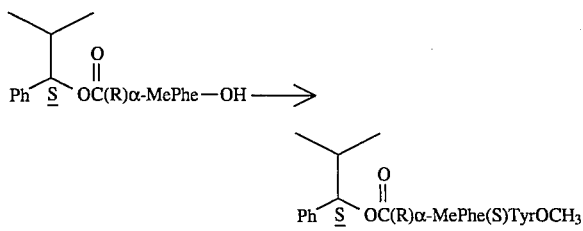

The acid (0.60 g, 1.7 mmol), HBTU (0.64 g, 1.7 mmol) and DIPEA (0.81 mL, 3.4 mmol) were stirred in DMF (10 mL) for 20 minutes. (S)-TyrOMe (0.33 g, 1.7 mmol) was added, and the mixture was stirred at room temperature for 16 hours. On removal of DMF, the residue was taken up in ethyl acetate (70 mL) and washed with 2M HCl (2×70 mL), 10% Na₂CO₃ (2×70 mL), and brine (70 mL). Drying (MgSO₄) and column chromatography on silica using 50% EtOAc:hexane gave a colorless oil (0.74 g, 82%).

IR (film): 3353, 2962, 1728, 1661, 1516, and 1230 cm⁻¹.

¹H NMR (CDCl₃): δ0.78 (3H, d, J=6.4 Hz, —CH₃), 0.95 (3H, d, J=6.4 Hz, —CH₃), 1.33 (3H, s, αCH₃), 2.00 (1H, m, (CH₃)₂C$\underline{H}$), 2.85–3.08 (3H, m, —C$\underline{H}_2$Ph—OH, Ph—C$\underline{H}$H), 3.29 (1H, d, J=12 Hz, PhCH$\underline{H}$), 3.69 (3H, s, CO₂Me), 4.76 (1H, m, αH), 4.98 (1H, s, Ar—O$\underline{H}$), 5.35–5.40 (2H, m, urethane, Ph—C$\underline{H}$OCO), and 6.64–7.40 (15H, m, Ar, amide).

m/e (CI): 133, 357, and 533.

Step 3

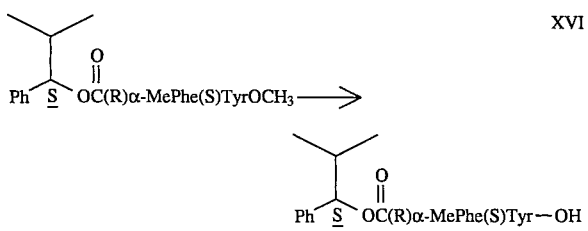

The methyl ester (0.73 g, 1.37 mmol) was dissolved in THF (20 mL), and a solution of lithium hydroxide monohydrate (0.086 g, 2.05 mmol) in water (5 mL) was added. The resulting solution was stirred vigorously for 60 hours. On removal of the solvents, the residue was partitioned between 2M HCl (50 mL) and ethyl acetate (70 mL). The aqueous layer was re-extracted with ethyl acetate (70 mL), and the combined organics were dried (MgSO₄). Further purification by column chromatography on silica using 50% ethyl acetate:hexane gave a white solid (0.49 g, 69%) (Intermediate XVI).

IR (film): 3391, 2965, 1706, 1695, 1652, 1515, and 1237 cm⁻¹.

¹H NMR (DMSO-d₆): 0.70 (3H, d, J=6.8 Hz, —CH₃), 0.82 (3H, d, J=6.4 Hz, —CH₃), 1.09 (3H, s, αCH₃), 2.82–3.30 (4H, m, PhC$\underline{H}_2$—, ArC$\underline{H}_2$—), 1.86–2.00 (1H, m, (CH₃)₂C$\underline{H}$), 4.10 (1H, m, αH), 5.22 (1H, d, PHC$\underline{H}$OCO), 6.50–7.50 (16H, m, Ar, amide, urethane), and 9.10 (1H, bs, ArO$\underline{H}$).

Step 4

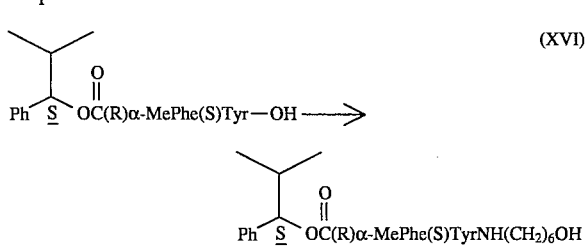

Example 12

The acid (0.080 g, 0.15 mmol) (Intermediate XVI), HBTU (0.057 g, 0.15 mmol), HOBT (catalytic amount), and 6-amino hexanol (0.018 g, 0.15 mmol) were dissolved in DMF (7 mL) and cooled to −10° C. DIPEA (0.072 mL, 0.30 mmol) was added, and the solution was stirred at −10° C. for 2 hours. On removal of DMF, the residue was taken up in ethyl acetate (70 mL) and washed with 2M HCl (2×50 mL), 10% Na₂CO₃ (2×50 mL) and brine (50 mL). Drying (MgSO₄) and further purification by column chromatography on silica using 5% methanol: dichloromethane gave a white solid (57 mg, 61%), mp=73°–78° C.

IR (film): 3332, 2934, 1698, and 1652 cm⁻¹.

¹H NMR (CDCl₃): δ0.73 (3H, d, J=6.8 Hz, —CH₃), 0.89 (3H, d, J=6.4 Hz, —CH₃), 1.20–1.65 (11H, m, αCH₃, —(CH₂)₄—), 2.03 (1H, m, (CH₃)₂C$\underline{H}$), 2.81 (1H, dd, C$\underline{H}$HAr), 3.04–3.88 (5H, m, C$\underline{H}_2$Ph, CH$\underline{H}$Ar, —NHC$\underline{H}_2$—), 3.68 (2H, t, J=6.0 Hz, CH₂—OH), 4.62 (1H, m, αH), 4.85 (1H, s, urethane), 5.21 (1H, d, J=8.0 Hz, PhC$\underline{H}$OCO), 6.38 (1H, d, amide), and 6.70–7.43 (16H, m, Ar, amide, ArO$\underline{H}$).

m/e (FAB): 281, 618, 550, and 355.

[α]$_D^{21.5°}$ $^C$=+48.86 (C=0.745, MeOH).

HPLC column:

C₁₈ Ultrasphere, 5µ, 4.6×250 mm solvent:

40–100% CH₃CN:H₂O+0.1% TFA over 30 minutes

R$_T$=14.6 minutes

Purity=98.9% (+1% S, R, R isomer).

Analysis calculated for C₃₆H₄₈N₃O₆.0.3 H₂O: C, 69.27; H, 7.85; N, 6.73. Found: C, 69.26; H, 7.58; N, 6.71.

SYNTHESIS OF EXAMPLE 13

{1-[1-(7-Hydroxy-heptylcarbamoyl)-2-(4-hydroxy-phenyl)-ethylcarbamoyl]-1-methyl-2-phenyl-ethyl}-carbamic acid 2-methyl-1-phenyl-propyl ester

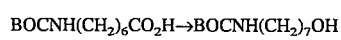

Step 1

Ethyl chloroformate (192 µL, 2 mmol) in dry THF (10 mL) was added dropwise over 20 minutes to a stirred solution of BOC NH(CH₂)₆CO₂H (450 mg, 1.8 mmol) and N-methylmorpholine (221 µL, 2 mmol) in THF (15 mL) cooled in an ice bath. The mixture was stirred for 1 hour and filtered. 2.0M Lithium borohydride in THF (3 mL, 6 mmol) was added dropwise to the filtrate cooled in an ice bath and allowed to warm to room temperature over 3 hours. The solvent was removed in vacuo, and the residue taken up in ethyl acetate (50 mL) and washed with water (3×40 mL) and dried (MgSO₄). Evaporation gave a colorless oil (395 mg, 95%).

IR (film: 3344, 2931, 2858, 1689, and 1531.

¹H NMR (CDCl₃): δ1.28–1.60 (19H, m, BOC CH₃×3, CH₂×5), 3.10 (2H, m, CONHC$\underline{H}$₂), 3.64 (2H, m, C$\underline{H}$₂OH), and 4.50 (1H, s, br urethane).

Step 2

BOCNH(CH₂)₇OH→TFA·H₂N(CH₂)₇OH (crude)

The BOC-aminoalcohol (280 mg, 1.2 mmol) was dissolved in dichloromethane (3 mL). Trifluoroacetic acid (3 mL) was added, and the mixture was stirred for 1 hour at room temperature. The solvent was removed in vacuo and the TFA azeotroped with toluene yielding a viscous oil (370 mg, 1.9 mmol TFA).

IR (film): 3420, 2925, 1755, and 1678 cm⁻¹.

Step 3

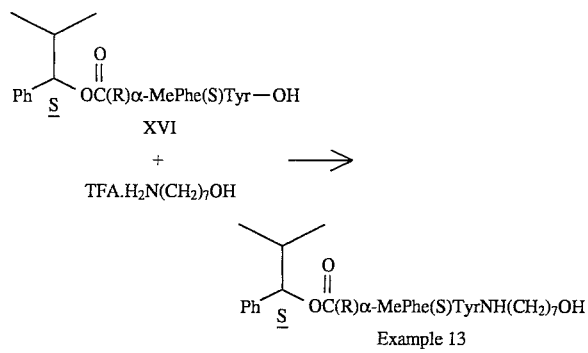

Example 13

The acid (0.080 g, 0.15 mmol) (Intermediate XVI), HBTU (0.057 g, 0.15 mmol), HOBT (catalytic amount), and the TFA salt (0.051 mg, 0.15 mmol) were dissolved in DMF (10 mL) and cooled to −10° C. DIPEA (0.109 mL, 0.45 mmol) was added, and the solution was stirred at −10° C. for 2 hours. Potassium carbonate (0.020 g, 0.15 mmol) in water (1 mL) was added, and the mixture was stirred vigorously at room temperature for a further 2 hours. On removal of the solvents, the residue was taken up in ethyl acetate (50 mL) and 2M HCl (50 mL). The organic layer was washed with 2M HCl (50 mL), 10% Na₂CO₃ (2×50 mL) and brine (50 mL) and dried (MgSO₄). Purification by column chromatography on silica using 5% methanol:dichloromethane gave a white solid (58 mg, 61%), mp=70°–76° C.

IR (film): 3334, 2933, 1699, and 1652 cm⁻¹.

¹H NMR (CDCl₃): δ0.72 (3H, d, J=6.8 Hz, CH₃), 0.88 (3H, d, J=6.8 Hz, —CH₃), 1.20–1.80 (13H, m, αCH₃, —(CH₂)₅—), 2.02 (1H, m, (CH₃)₂C$\underline{H}$), 2.76–3.80 (8H, m, PhC$\underline{H}$₂, ArC$\underline{H}$₂, NHC$\underline{H}$₂, C$\underline{H}$₂—OH), 4.62 (1H, m, αH), 4.83 (1H, s, urethane), 5.19 (1H, d, J=8.4 Hz, PhC$\underline{H}$OCO), 6.40 (1H, d, amide), and 6.70–7.40 (16H, m, Ar, amide, Ar—O$\underline{H}$).

m/e (FAB): 267, 456, 550, and 632.

[α]$_D^{23}$=+47.05 (C=0.88,MeOH).

HPLC column: Ultrasphere C₁₈, 5µ, 4.6×250 mm solvent:

40–100% CH₃CN:H₂O+0.1% TFA. 1 mL/min over 30 minutes

R$_T$=15.7 minutes

Purity=99.1% (+0.8% S, R, R, isomer).

Analysis calculated for C₃₇H₅₀N₃O₆·0.3 H₂O: C, 69.63; H, 7.99; N, 6.58. Found:. C, 69.53; H, 7.81; N, 6.57.

SYNTHESIS OF INTERMEDIATE XVII

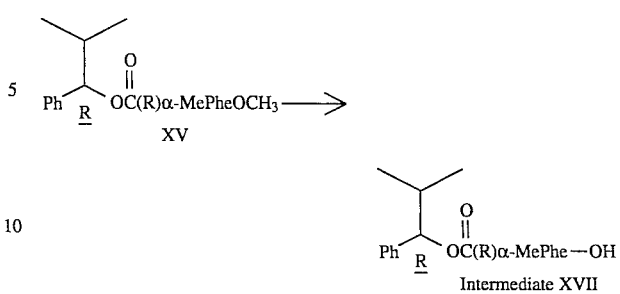

Intermediate XVII

The methyl ester (1.50 g, 4.06 mmol) (Intermediate XV) was taken up in THF (20 mL). Lithium hydroxide monohydrate (0.34 g, 8.12 mmol) in water (5 mL) was added, and the resulting mixture was heated at reflux for 24 hours. On removal of the solvents, the residue was partitioned between 2M HCl (70 mL) and ethyl acetate (70 mL). The aqueous layer was re-extracted with ethyl acetate (70 mL), and the combined organics were dried (MgSO₄). Purification by column chromatography using 50% ethyl acetate:hexane gave the acid as a white foam (0.82 g, 57%).

IR (film): 3032, 2964, 1711, 1497, 1452, and 1078 cm⁻¹.

¹H NMR (CDCl₃): δ0.81 (3H, d, J=6.8 Hz, —CH₃), 0.99 (3H, d, J=6.8 Hz, —CH₃), 2.08 (1H, m, (CH₃)₂C$\underline{H}$), 3.14 (1H, d, J=13.6 Hz, PhC$\underline{HH}$), 3.37 (1H, d, J=12.4 Hz, PhCH$\underline{H}$), 5.36 (1H, d, J=6.8 Hz, PhC$\underline{H}$OCO), 5.44 (1H, s, urethane), and 6.82–7.40 (10H, m, Ar).

m/e (CI): 133, 180, 224, and 356.

SYNTHESIS OF EXAMPLE 14

Carbamic acid,
[1-methyl-2-oxo-2-[(1-phenylethyl)amino]-1-(phenylmethyl)ethyl]-, (R) or
(S)-2-methyl-1-phenylpropyl ester, [R-(R*,S,*)]-

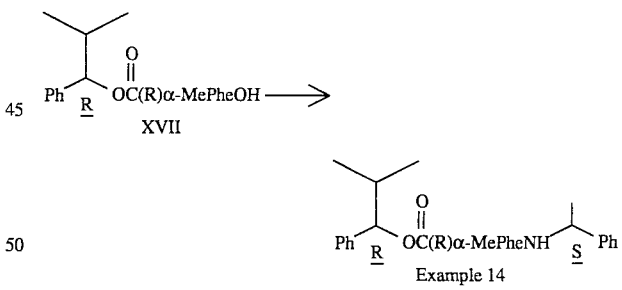

Example 14

DCCI (29 mg, 0.14 mmol) was added to a stirred solution of the acid (46 mg, 0.13 mmol) (Intermediate XVII) and HOBT H₂O (25 mg, 0.16 mmol) in ethyl acetate (2 mL) at room temperature and stirred for 2 hours. The mixture was filtered and the solid washed with ethyl acetate (3 mL). The filtrate was added to (S)-α-methylbenzylamine (23 mg, 0.19 mmol) in ethyl acetate (1 mL) and the mixture stirred for 26 hours. The solution was washed with 5% citric acid (2×10 mL), saturated NaHCO₃ (2×10 mL) and brine (10 mL), dried (MgSO₄), and filtered. The solution was cooled to −10° C. for 2 hours and filtered. Evaporation gave a white solid (41 mg, 70%), mp 151°–161° C.

IR (film): 3326, 3031, 2930, 1721, 1694, 1645, 1485, and 1078 cm⁻¹.

¹H NMR (CDCl₃): δ0.81 (3H, d, J=6.8 Hz, —CH₃), 0.98 (3H, d, J=6.6 Hz, —CH₃), 1.32 (3H, d, J=6.8 Hz, —CH₃), 2.02–2.11 (1H, m, (CH₃)₂C$\underline{H}$), 3.14 (1H, d, J=13.9 Hz, PhC$\underline{HH}$), 3.28 (1H, d, J=13.4 Hz, PhC$\underline{HH}$), 4.93–5.00 (1H, m, CH₃C$\underline{H}$NHCO), 5.26 (1H, b, urethane), 5.38 (1H, d, J=7.6 Hz, PhC$\underline{H}$OCO), 6.39 (1H, d, J= 7.1 HZ, amide), 6.99–7.01 (2H, m, Ar), and 7.14–7.36 (13H, m, Ar).

m/e (CI): 133, 283, 327, and 459.

[α]$_D^{20}$=+10.3° (C=0.53, acetone).

Analysis calculated for C₂₉H₃₄N₂O₃.0.25 H₂O: C, 75.21; H, 7.51; N, 6.05. Found: C, 75.42; H, 7.60; N, 6.31.

SYNTHESIS OF EXAMPLE 15

[1-Methyl-1-(1-methyl-1-phenyl-ethylcarbamoyl)-2-phenyl-ethyl]-carbamic acid 2-methyl-1-phenyl-propyl ester

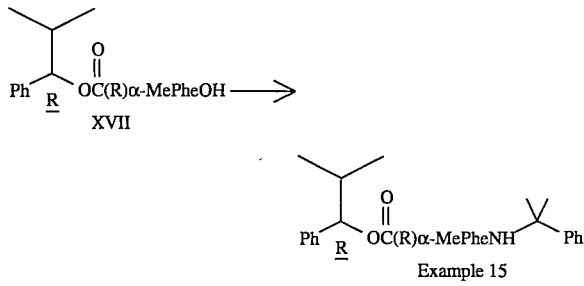

Example 15

The acid (50 mg, 0.14 mmol) (Intermediate XVII), HBTU (53 mg, 0.14 mmol) and DIPEA (24.5 µL, 0.14 mmol) were dissolved in DMF (3 mL) and stirred for 5 minutes. Cumylamine (20 mg, 0.15 mmol) and DIPEA (24.5 µL, 0.14 mmol) were added, and the solution was stirred overnight. On removal of the solvent, the residue was dissolved in ethyl acetate (50 mL) and washed with 1M HCl (3×30 mL), saturated NaHCO₃ (3×30 mL), water (30 mL) and brine (30 mL), and dried (MgSO₄). Evaporation and purification of the residue by column chromatography using 25% ethyl acetate:heptane gave a white foam (57 mg, 86%), mp=115°–123° C.

IR (film): 3285, 2975, 1716, 1668, and 1496 cm⁻¹.

¹H NMR (CDCl₃): δ0.82 (3H, d, J=6.4 Hz, C$\underline{H_3}$CHCH₃), 1.00 (3H, d, J=6.4 Hz, CH₃CHC$\underline{H_3}$), 1.41 (3H, s, αCH₃), 1.52 (6H, s, CH₃×2), 2.08 (1H, m, CH₃C$\underline{H}$CH₃), 3.12 (1H, d, J=14 Hz, PhC$\underline{HH}$), 3.34 (1H, d, J=14 Hz, PhC$\underline{HH}$), 5.16 (1H, s, urethane), 5.40 (1H, d, J= 7.6 Hz, PhC$\underline{H}$OCO), 6.39 (1H, s, amide), and 7.04–7.35 (15H, m, Ar).

m/e (APCI): 473.5 MH⁺.

HPLC: 60–100% B over 20 minutes. A=H₂O, B=CH₃CN +0.1% TFA. R$_T$=16.51 minutes (98%)

Analysis calculated for C₃₀H₃₆N₂O₃: C, 76.24; H, 7.68; N, 5.93. Found: C, 76.03; H, 7.64; N, 6.01.

SYNTHESIS OF EXAMPLE 16

[1-(2-Hydroxy-1-phenyl-ethylcarbamoyl)-1-methyl-2-phenyl-ethyl]-carbamic acid 2-methyl-1-phenyl-propyl ester

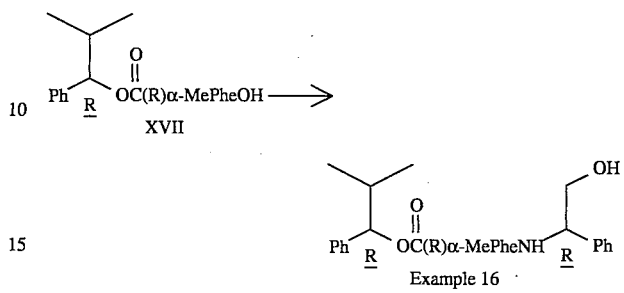

Example 16

DIPEA (36 mg, 0.20 mmol) was added to a solution of the acid (50 mg, 0.14 mmol) (Intermediate XVII), HBTU (53 mg, 0.14 mmol) and (R)-2-phenylglycinol (19 mg, 0.14 mmol) in DMF (3 mL). The reaction mixture was stirred overnight at room temperature and then evaporated to dryness. The residue was partitioned between ethyl acetate and 0.1M HCl. Further purification by column chromatography on silica using 40% ethyl acetate:hexane yielded an amorphous white solid (60 mg, 90%), mp=124°–130° C.

IR (film): 3395, 2963, 1706, 1659, 1495, and 1079 cm⁻¹.

¹H NMR (CDCl₃): δ0.81 (3H, d, J=8 Hz), 0.98 (3H, d, J=8 Hz), 1.48 (3H, s), 2.04 (1H, m), 3.09 and 3.30 (2H, ABq, J=15 Hz), 3.70 (2H, m), 4.95 (1H, m), 5.24 (1H, s), 5.38 (1H, d, J=7 Hz), 6.93 (1H, d, J= 7 Hz), 7.04 (2H, m), 7.12 (2H, m), and 7.20–7.30 (1H, m).

Analysis calculated for C₂₉H₃₄N₂O₄: C, 73.39; H, 7.22; N, 5.90. Found: C, 73.11; H, 7.23; N, 5.72.

SYNTHESIS OF EXAMPLE 17

[1-Methyl-2-phenyl-1-(1-phenyl-ethylcarbamoyl)-ethyl]-carbamic acid 1-(4-fluoro-phenyl)-2-methyl-propyl ester

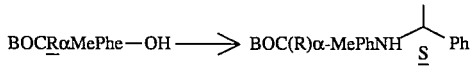

Step 1

DCCI (0.81 g, 3.9 mmol) was added to a stirred solution of BOC (R)-α-MePheOH (1.0 g, 3.58 mmol) and HOBT.H₂O (0.69 g, 4.48 mmol) in ethyl acetate (100 mL) at room temperature and stirred for 2 hours. The reaction mixture was filtered, and a solution of (S)-α-methylbenzylamine (0.65 g, 5.37 mmol) in ethyl acetate (25 mL) was added dropwise over 30 minutes. The mixture was stirred for 16 hours, extracted with 10% citric acid solution (2×25 mL), saturated NaHCO₃ (25 mL) and once with brine (25 mL), and dried (MgSO₄). Further purification by column chromatography on silica using 25% ethyl acetate:hexane yielded a solid (1.23 g, 90%), mp=154° C.

IR (film): 3329, 2975, 1684, 1646, and 1519 cm⁻¹.

¹H NMR (CDCl₃): δ1.41 (3H, s, CH₃), 1.44 (9H, s, C(C$\underline{H_3}$)₃), 1.48 (3H, d, J=6.8 Hz, C$\underline{H_3}$CH), 3.07 (1H, d, J=13.6 Hz, PhC$\underline{HH}$), 3.42 (1H, d, J=13.6 Hz, PhC$\underline{HH}$), 4.73 (1H, b, N$\underline{H}$CO₂—), 5.09–5.13 (1H, m, PhC$\underline{H}$(CH₃)NH), 6.60 (1H, b, CON$\underline{H}$), 7.09–7.11 (2H, m, Ar), and 7.23–7.33 (8H, m, Ar).

m/e (CI): 383, 327, 283, 178, and 134.

$[\alpha]_D^{20}$=+28.2 (C=1.15, acetone).

Analysis calculated for $C_{23}H_{30}N_2O_3 \cdot 0.1\ H_2O$: C, 71.14; H, 7.84; N, 7.22. Found: C, 71.04; H, 7.78; N, 7.14.

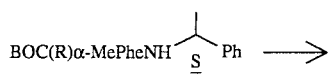

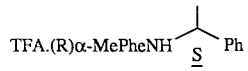

Step 2

The BOC protected amine (500 mg, 1.31 mmol) was dissolved in dichloromethane:TFA (5 mL, 1:1 mixture) and stirred at room temperature for 1 hour. The solvents were removed in vacuo, and diethyl ether was added to the resulting syrup to precipitate a white solid (493 mg, 95%).

IR (film): 3269, 3066, 2561, 1668, 1202, and 1135 cm$^{-1}$.

$^1$H NMR (DMSO-d$_6$): δ1.38 (3H, d, J=6.8 Hz, C$\underline{H}_3$CH), 1.50 (3H, s, C$\underline{H}_3$), 3.04 (1H, d, J=14.0 Hz, PhCH$\underline{H}$), 3.22 (1H, d, J=14.4 Hz, PhC$\underline{H}$H), 4.89–4.93 (1H, m, CH$_3$C$\underline{H}$) 7.17–7.34 (10H, m, Ar) 8.04 (3H, b, $^+$N$\underline{H}_3$), and 8.67 (1H, d, J=7.6 Hz, CON$\underline{H}$CH).

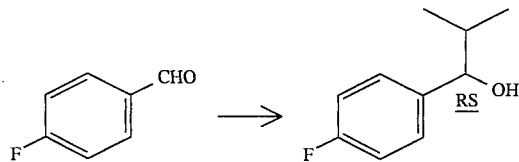

Step 3

A solution of 2.0M isopropyl magnesium chloride (6.0 mn, 12.0 mmol) in ether was added dropwise over 5 minutes to a stirred solution of p-fluorobenzaldehyde (1.01 g, 8.15 mmol) in ether (20 mL) cooled in an ice water bath and stirred for 20 minutes. The mixture was stirred at room temperature for 40 minutes and quenched with 10% citric acid solution (25 mL). The layers were separated, and the aqueous solution was re-extracted with ether (2×25 mL). The combined ether extracts were washed with brine (25 mL) and dried (MgSO$_4$). Evaporation and further purification by column chromatography on silica using 30% diethyl ether:hexane yielded the alcohol (0.97 g, 71%).

IR (film): 3379, 2962, 2874, 1605, 1510, 1224, and 1157 cm$^{-1}$.

$^1$H NMR (CDCl$_3$): δ0.78 (3H, d, J=7.2 Hz, C$\underline{H}_3$CHCH$_3$), 0.99 (3H, d, J=6.8 Hz, CH$_3$CHC$\underline{H}_3$), 1.85 (1H, b, CH—O$\underline{H}$), 1.86–1.96 (1H, m, CH$_3$C$\underline{H}$CH$_3$), 4.35 (1H, d, J=6.8 Hz, Ar C$\underline{H}$OH), 7.00–7.05 (2H, m, Ar), and 7.25–7.30 (2H, m, Ar).

m/e (CI): 151, 125, 109, and 97.

Analysis calculated for $C_{10}H_{13}FO$: C, 71.40; H, 7.79; N, 11.29. Found: C, 71.17; H, 7.70; N, 10.99.

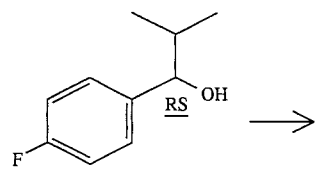

Step 4

Pyridine (0.44 mL, 5.44 mmol) in anhydrous dichloromethane (10 mL) was added dropwise over 50 minutes to a solution of the alcohol (0.823 g, 4.95 mmol) and p-nitrophenylchloroformate (1.10 g, 5.44 mmol) in anhydrous dichloromethane (10 mL) cooled in an ice water bath. The solution was allowed to warm to room temperature and stirred for 20 hours. The solvent was removed in vacuo and the residue taken up in diethyl ether (50 mL), washed with 10% citric acid solution (2×25 mL) and brine (25 mL), and dried (MgSO$_4$). Evaporation and further purification by column chromatography on silica using 10% ether:hexane gave the carbonate (1.35 g, 82%).

IR (film): 2968, 1765, 1526, 1347, 1255, 1217, and 1160 cm$^{-1}$.

$^1$H NMR (CDCl$_3$): δ0.83 (3H, d, J=6.8 Hz, CH$_3$CHC$\underline{H}_3$), 1.10 (3H, d, J=6.8 Hz, C$\underline{H}_3$CHCH$_3$), 2.19–2.25 (1H, m, CH$_3$C$\underline{H}$CH$_3$), 5.34 (1H, d, J=8.0 Hz, ArC$\underline{H}$O—), 7.06–7.10 (2H, m, Ar), 7.31–7.36 (4H, m, Ar), and 8.25 (2H, d, J=8.4 Hz, Ar).

Analysis calculated for $C_{17}H_{16}FNO_5$: C, 61.26; H, 4.84; N, 4.20; F, 5.70. Found: C, 61.30; H, 4.90; N, 4.11; F, 5.68.

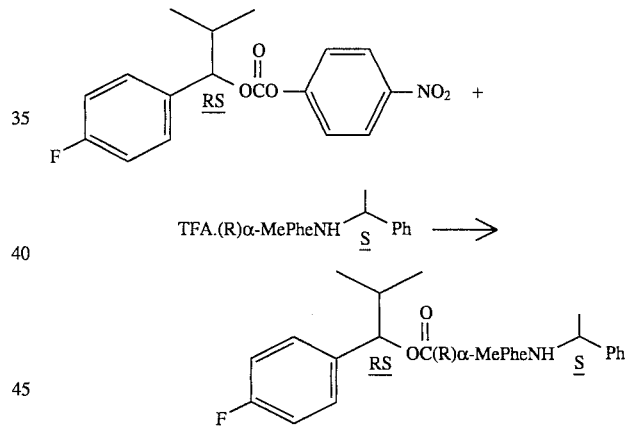

Example 17

Step 5

DMAP (31 mg, 0.25 mmol) was added to a solution of the amine salt (75 mg, 0.189 mmol) and carbonate (76 mg, 0.227 mmol) in DMF (5 mL) and stirred at room temperature for 1 day. Additional carbonate (41 mg, 0.123 mmol) was added and stirring continued for 3 days. The reaction mixture was diluted with ethyl acetate (50 mL) and washed with 10% potassium carbonate solution (6×25 mL) and brine (25 mL). Drying (MgSO$_4$) and chromatography on silica using 25% EtOAc:hexane followed by preparative HPLC using 70% to 90% CH$_3$CN:H$_2$O gave the product (1.5 mg, 2%), mp 142°–165° C.

IR (film): 3330, 2922, 1671, 1439, 1203, and 1135 cm$^{-1}$.

$^1$H NMR (CDCl$_3$): δ0.76–079 (3H, m, C$\underline{H}_3$), 0.93–0.98 (3H, m, C$\underline{H}_3$), 1.26–1.49 (6H, m, 2×C$\underline{H}_3$), 1.99–2.05 (1H, m, CH$_3$C$\underline{H}$CH$_3$), 3.08–3.33 (2H, m, PhC$\underline{H}$H), 4.98–5.06 (1H, m, PhC$\underline{H}$NHCO), 5.21 and 5.34 (1H, 2s, OCON$\underline{H}$), 5.35 (1H, d, J=7.6 Hz, PhC$\underline{H}$O—), 6.29–6.35 (1H, m, CON$\underline{H}$), 6.93–7.04 (4H, m, Ar), and 7.12–7.34 (10H, m, Ar).

m/e (CI): 477, 283, and 151.
HPLC: 99.7%.

We claim:

1. A compound of formula

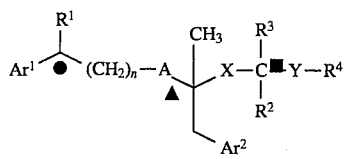

or a pharmaceutically acceptable salt thereof
wherein:
the ●, ▲, and ■ indicate all stereoisomers at these carbon atoms;
$Ar^1$ is phenyl unsubstituted or substituted by from 1 to 3 substituents selected from:
alkyl,
halogen,
nitro,
trifluoromethyl,
cyano,
hydroxy, and
alkoxy;
$Ar^1$ can also be pyridine;
$R^1$ is hydrogen or a straight, branched, or cycloalkyl of from 1 to 7 atoms; or
$Ar^1$ and $R^1$ form a ring of 5 to 8 atoms when joined by a bond;
n is an integer of from 0 to 2;
A is OCONH, CONH, $CO_2$, NHCONH, $CH_2NH$, and $COCH_2$;
$Ar^2$ is phenyl as defined in $Ar^1$ above,
pyridine,
thiophene,
naphthyl,
indole,
benzofuran,
benzothiophene, or
imidazole;
X is
—OCONH—,
—CONH—,
—$CO_2$—,
—NHCONH—,
—$CH_2NH$—,
—$COCH_2$—,
—$CONCH_3$—,
—$CH_2O$—,
—$CH_2CH_2$—, or
—CH=CH—;
$R^2$ is
hydrogen,
methyl,
phenyl,
benzyl,
$CH_2C_6H_{11}$, or

$R^3$ is hydrogen or methyl;
Y is
—$(CH_2)_m$—,
—$(CH_2)_mO$—, wherein m is an integer of from 1 to 5,
—CONH—,
—$CH_2NH$—,
—$COCH_2$—, or
—CH=CH—; and
$R^4$ is hydrogen, alkyl straight or branched of from 1 to 8 atoms unsubstituted or substituted by a substituent selected from:
hydrogen,
$OR^5$,
$NHCOCH_3$,
$NR^5R^6$,
$SO_2CH_3$,
$SO_2NH_2$,
$NHSO_2NH_2$,
$NHCONH_2$,
$CONR^5R^6$,
$COR^5$,

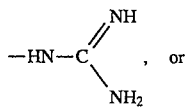, or

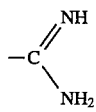

wherein $R^5$ and $R^6$ are each independently hydrogen or alkyl, and
$R^4$ is

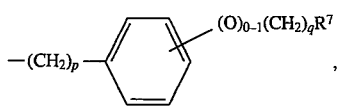,

,

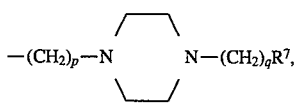,

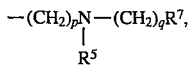,

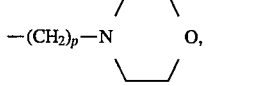,

—$CH_2O(CH_2)_pO(CH_2)_qR^7$, or

—$(CH_2)_p$—$O(CH_2)_qR^7$ wherein p is an integer of from 0 to 5, q is an integer of from 0 to 4, and $R^7$ is hydrogen, hydroxy, alkoxy, $CONR^5R^6$, or $NHCONR^5R^6$ wherein $R^5$ and $R^6$ are as described above.

2. A compound according to claim 1 wherein:
● is S or R, ▲ is R, and ■ is S;
$Ar^1$ is phenyl unsubstituted or substituted with from 1 to 2 substituents selected from:
alkyl,
halogen,
cyano, and alkoxy;

R¹ is a straight, branched, or cyclic alkyl of from 1 to 6 atoms; or

Ar¹ and R¹ form a ring of 7 atoms;

n is an integer of from 0 to 1;

A is OCONH, CONH, NHCONH, or CH₂NH;

A² is phenyl as defined in Ar¹ above,
pyridine,
thiophene,
naphthyl, or
benzofuran;

X is
OCONH,
NHCONH,
CH₂NH,
CONCH₃, or
COCH₂;

R² is
hydrogen,
phenyl,
benzyl, or

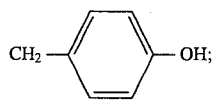

R³ is hydrogen or methyl;

Y is (CH₂)$_m$, CONH, CH₂NH, or COCH₂;

R⁴ is hydrogen, alkyl straight or branched of from 3 to 7 atoms with a substituent selected from:
OR⁵,
NHCOCH₃,
SO₂CH₃,
SO₂NH₂,
NHSO₂NH₂,
NHCONH₂,
CONR⁵R⁶,
COR⁵ wherein R⁵ and R⁶ are each independently hydrogen or alkyl, and

R⁴ is

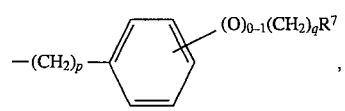

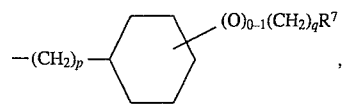

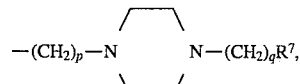

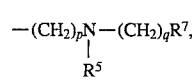

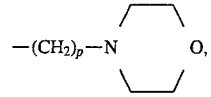

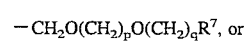

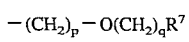

wherein p is an integer of from 0 to 2, q is an integer of from 0 to 3, and R⁷ is hydroxy, alkoxy, CONR⁵R⁶, or NHCONR⁵R⁶.

3. A compound according to claim 1 wherein

● is S or R, ▲ is R, and ■ is S;

Ar¹ is phenyl unsubstituted or substituted by halogen, cyano, or alkyl;

R¹ is a branched or cycloalkyl of from 3 to 6 carbon atoms, or Ar¹ and R¹ are joined to form a ring of 7 atoms;

n is zero;

A is OCONH or NHCONH;

Ar² is phenyl unsubstituted or substituted by halogen, cyano or alkyl, or

Ar² is thiophene, naphthyl, or benzofuran;

X is CONH, CH₂NH, or COCH₂;

R² is hydrogen, phenyl or

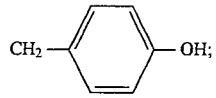

R³ is hydrogen or methyl;

Y is CH₂ or CONH; and

R⁴ is hydrogen, alkyl which is a straight chain of from 4 to 6 atoms with a substituent selected from:
hydroxy,
NHCOCH₃, or
NHCONH₂.

4. A compound according to claim 1 and selected from:

Carbamic acid, [2-[(9-amino-9-oxononyl)-amino]-1-methyl-2-oxo-1-(phenylmethyl)ethyl]-, 2-methyl-1-phenylpropyl ester, [R-(R*,S*)]-;

Carbamic acid, [2-[(9-amino-9-oxononyl)-amino]-1-methyl-2-oxo-1-(phenylmethyl)ethyl]-, 1-(4-chlorophenyl)-2-methylpropyl ester;

[1-(8-Carbamoyl-octylcarbamoyl)-1-methyl-2-phenylethyl]-carbamic acid cyclopentyl-phenyl-methyl ester;

[1-(8-Carbamoyl-octylcarbamoyl)-1-methyl-2-phenylethyl]-carbamic acid 6,7,8,9-tetrahydro-5H-benzocyclohepten-5-yl ester; and

[1-(8-Carbamoyl-octylcarbamoyl)-1-methyl-2-phenylethyl]-carbamic acid 2,2-dimethyl-1,2,3,4-tetrahydronaphthalen-1-yl ester.

5. A compound according to claim 1 and selected from:

Carbamic acid, [1-methyl-2-oxo-2-[(1-phenylethyl)amino]-1-(phenylmethyl)ethyl]-, (R) or (S)-2-methyl-1-phenylpropyl ester, [R-(R*,S*)]-;

[1-Methyl-1-(1-methyl-1-phenyl-ethyl-carbamoyl)-2-phenyl-ethyl]-carbamic acid 2-methyl-1-phenyl-propyl ester; and

[1-(2-Hydroxy-1-phenyl-ethylcarbamoyl)-1-methyl-2-phenyl-ethyl]-carbamic acid 2-methyl-1-phenyl-propyl ester.

6. A compound according to claim 1 and selected from:

Carbamic acid, [2-[(8-hydroxyoctyl)amino]-1-(1H-indol-3-ylmethyl)-1-methyl-2-oxoethyl]-, 2-methyl-1-phenylpropyl ester;

[2-(2-Fluoro-phenyl)-1-methyl-1-(7-ureido-heptylcarbamoyl)-ethyl]-carbamic acid 2-methyl-1-phenyl-propyl ester;

[2-(2,3-Difluoro-phenyl)-1-methyl-1-(7-ureido-heptylcarbamoyl)-ethyl]-carbamic acid 2-methyl-1-phenyl-propyl ester; and

[1-(8-Carbamoyl-octylcarbamoyl)-1-methyl-2-phenyl-ethyl]-carbamic acid 6,6-dimethyl- 6,7,8,9-tetrahydro-5H-benzocyclohepten-5-yl ester.

7. A compound according to claim 1 and selected from:

{1-[1-(6-Hydroxy-hexylcarbamoyl)- 2-(4-hydroxy-phenyl)-ethylcarbamoyl]-1-methyl-2-phenyl-ethyl}-carbamic acid 2-methyl-1-phenyl-propyl ester;

{1-[1-(7-Hydroxy-heptylcarbamoyl)-2-(4-hydroxy-phenyl)-ethylcarbamoyl]-1-methyl-2-phenyl-ethyl}-carbamic acid 2-methyl-1-phenyl-propyl ester; and {1-[2-(4-Hydroxy-phenyl)-1-(6-ureido-hexylcarbamoyl)-ethylcarbamoyl]-1-methyl-2-phenyl-ethyl}-carbamic acid 2-methyl-1-phenyl-propyl ester.

8. A pharmaceutical composition comprising a therapeutically effective amount of a compound according to claim 1 and a pharmaceutically acceptable carrier.

9. A method for treating central nervous system disorders in a mammal comprising administering the composition according to claim 1 to said mammal.

10. A method for treating gastrointestinal disorders in a mammal comprising administering the composition according to claim 1 to said mammal.

11. A method for treating respiratory disorders in a mammal comprising administering the composition according to claim 1 to said mammal.

12. A method for treating inflammation disorders in a mammal comprising administering the composition according to claim 1 to said mammal.

13. A method for treating circulatory insufficiency disorders in a mammal comprising administering the composition according to claim 1 to said mammal.

14. A method for antagonizing the effects of NKB at $NK_3$ receptors in a mammal comprising administering a compound according to claim 1 to said mammal.

* * * * *

UNITED STATES PATENT AND TRADEMARK OFFICE
CERTIFICATE OF CORRECTION

PATENT NO. : 5,554,641
DATED : Sep. 10, 1996
INVENTOR(S) : Horwell et al.

It is certified that error appears in the above-identified patent and that said Letters Patent is hereby corrected as shown below:

Column 59, line 45, remove [—$CO_2$—,] between "—CONH—," and "—NHCONH—,"

Column 61, line 15, insert --CONH,-- between "OCONH," and "NHCONH,".

Signed and Sealed this

Ninth Day of May, 2000

Q. TODD DICKINSON

*Attest:*

*Attesting Officer*     *Director of Patents and Trademarks*